(12) United States Patent
Thompson et al.

(10) Patent No.: US 10,118,996 B2
(45) Date of Patent: Nov. 6, 2018

(54) POLYROTAXANES AND USES THEREOF

(71) Applicant: Purdue Research Foundation, West Lafayette, IN (US)

(72) Inventors: David H. Thompson, West Lafayette, IN (US); Seok-Hee Hyun, West Lafayette, IN (US); Kyle J. Wright, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 694 days.

(21) Appl. No.: 13/774,302

(22) Filed: Feb. 22, 2013

(65) Prior Publication Data

US 2013/0224881 A1    Aug. 29, 2013

Related U.S. Application Data

(60) Provisional application No. 61/602,835, filed on Feb. 24, 2012.

(51) Int. Cl.
| | |
|---|---|
| *C08G 83/00* | (2006.01) |
| *G01N 33/58* | (2006.01) |
| *C08B 37/16* | (2006.01) |
| *C08H 1/00* | (2006.01) |

(52) U.S. Cl.
CPC ........ *C08G 83/007* (2013.01); *C08B 37/0012* (2013.01); *C08B 37/0015* (2013.01); *C08H 1/00* (2013.01); *G01N 33/58* (2013.01)

(58) Field of Classification Search
None
See application file for complete search history.

(56) References Cited

U.S. PATENT DOCUMENTS

| 2001/0041172 A1* | 11/2001 | Bentley et al. | ............ 424/78.19 |
| 2004/0162275 A1* | 8/2004 | Yui et al. | ................. 514/183 |
| 2009/0011933 A1* | 1/2009 | Ito et al. | ................. 502/402 |

OTHER PUBLICATIONS

Supporting Information for Hyun et al., "Oriented Insertion of phi29 N-Hexahistidine-tagged gp10 Connector Protein Assemblies into C20BAS Bolalipid Membrane Vesicles," J. Am. Chem. Soc., 2010, vol. 132, No. 48, pp. 17053-17055 (IDS submitted Apr. 12, 2015).*
Levert et al., "A Biotin Analog Inhibits Acetyl-CoA Carboxylase Activity and Adipogenesis," J. Biol. Chem., 2002, vol. 277, No. 19, pp. 16347-16350.*
Flora et al., "Chelation in Metal Intoxication," Int. J. Environ. Res. Public Health, 2010 vol. 7, No. 7, pp. 2745-2788.*
Methods in Enzymol., Eds. Richard & Deutscher 2009, vol. 463, p. 445.*
Harada et al., "Preparation and Characterization of a Polyrotaxane Consisting of Monodisperse Poly(ethylene glycol) and α-Cyclodextrins," J. Am. Chem. Soc., 1994, vol. 116, No. 8, pp. 3192-3196.*
Cheng et al. "The Advent of Near-Atomic Resolution in Single-Particle Electron Microscopy", *Ann. Rev. Biochem.* 2009, 78, 723-742.
Cong et al. "4.0-Å resolution cryo-EM structure of the mammalian chaperonin TRiC/CCT reveals its unique subunit arrangement", *P Natl Acad Sci USA* 2010, 107, 4967.
Grey et al. "Challenges and Opportunities for New Protein Crystallization Strategies in Structure-Based Drug Design", *Curr. Op. Drug Disc.* 2010, 5, 1039.
Hyun et. al. "Oriented Insertion of phi29 N-Hexahistidine-tagged gp10 Connector Protein Assemblies into C20BAS Bolalipid Membrane Vesicles", *J. Am. Chem. Soc.* 2010, 132, 17053.
Loethen et al. "Synthesis, characterization, and pH-triggered dethreading of alpha-cyclodextrin-poly(ethylene glycol) polyrotaxanes bearing cleavable endcaps", *Biomacromolecules*, 2006, 7, 2501.
Ohya et al. "Polyrotaxane composed of poly-L-lactide and alpha-cyclodextrin exhibiting protease-triggered hydrolysis", *Bimacromolecules*, 2009, 10, 2261.
Singh et al. "Folate and Folate—PEG-PAMAM Dendrimers: synthesis, characterization, and targeted anticancer drug delivery potential in tumor bearing mice", *Bioconjug. Chem.* 2008, 19, 2239-2252.
Susumu et al. "Multifunctional ligands based on dihydrolipoic acid and polyethylene glycol to promote biocompatibility of quantum dots", *Nat. Protoc.* 2009, 4, 424-436.
Yang et al. "Novel Supramolecular Block Copolymer: A Polyrotaxane Consisting of Many Threaded α- and γ-Cyclodextrins with an ABA Triblock Architecture", *Macromolecules*, 2009, 42, 3856-3859.

* cited by examiner

*Primary Examiner* — Galina Yakovleva
(74) *Attorney, Agent, or Firm* — Mark S. Cohen; Pearl Cohen; Zedek Latzer Baratz LLP

(57) ABSTRACT

A polyrotaxane containing an affinity binding group has been designed and prepared. The polyrotaxane of the invention can be used for characterization and determination of the three-dimensional structures of biological molecules, such as proteins.

8 Claims, 11 Drawing Sheets
(8 of 11 Drawing Sheet(s) Filed in Color)

Scheme 1. Synthesis of Lys-NTA-α-CD:PEG10K polyrotaxane

Scheme 3. Synthesis of NTA-modified-α-CD:biotin-PEG-biotin:SA Polyrotaxane Hydrogel Scheme 4. Synthesis of NTA-modified-α-CD:HS-PEG-SH:4,8-arm-PEG-MAL polyrotaxane hydrogel

POLYROTAXANES AND USES THEREOF

CROSS REFERENCE TO RELATED APPLICATIONS

This application claims the benefit of U.S. Provisional Application Ser. No. 61/602,835, filed on Feb. 24, 2012, which is incorporated herein by reference in its entirety.

GOVERNMENT INTEREST STATEMENT

This invention was made with government support under R21GM079058 and R41GM098017 awarded by the National Institutes of Health. The government has certain rights in the invention.

TECHNICAL FIELD

The invention relates to polyrotaxanes, methods of preparation thereof, and uses thereof for characterization and determination of the three-dimensional structures of biological molecules, such as proteins.

BACKGROUND OF THE INVENTION

XRD and NMR based methods account for the majority of the high-resolution protein structures to date (Grey, J.; Thompson, D. H. *Curr. Op. Drug Disc.* 2010, 5, 1039). These methods, however, are of limited utility for structure determination of integral membrane proteins (IMP) and multiprotein complexes. Cryogenic electron microscopy (cryo-EM) has become an increasingly powerful method for determining the three-dimensional structures of proteins and their assemblies via Single Particle Analysis (SPA) (Cheng, et al. *Ann. Rev. Biochem.* 2009, 78, 723). Unlike other electron microscopy techniques, cryogenic electron microscopy (cryo-EM) does not require staining or embedding in non-physiological media. Recently, the technique has been used to determine protein structural information at 4.0 Å resolution (Cong et al. *P Natl Acad Sci USA* 2010, 107, 4967).

A key challenge for protein structural determination via cryogenic electron microscopy (cryo-EM) is that the method requires the collection of more than 30,000 images to enable image reconstruction at resolutions below ~10 Å. Since protein concentrations for Single Particle Analysis (SPA) are typically in the μg-mg/mL range, data collection is a laborious and time-consuming process because there are typically only a few particles in the field of view at the magnification required to image the nano-scale targets. Thus, there is an ongoing need for the development of methods that increase the probability of finding the target particles in a vitrified sample to accelerate Single Particle Analysis (SPA) by cryogenic electron microscopy (cryo-EM).

SUMMARY OF THE INVENTION

In one aspect, the invention features a polyrotaxane that comprises a plurality of to macrocyclic molecules, a linear axle molecule that can thread through the macrocyclic molecules, and a capping group at each end of the linear axle molecule, in which one or more of the macrocyclic molecules comprise an affinity binding group and in which the macrocyclic molecules can be laterally and rotationally mobile along the linear axle molecule.

In another aspect, the invention provides a crosslinked polyrotaxane that comprises two or more of polyrotaxanes, wherein said polyrotaxanes each comprise a plurality of macrocyclic molecules and a linear axle molecule threading through the macrocyclic molecules, wherein one or more of the macrocyclic molecules comprise an affinity binding group and are laterally and rotationally mobile along the linear axle molecule, and wherein the linear axle molecule is crosslinked with another linear molecule.

In another aspect, the present invention provides a method of characterizing or determining a three-dimensional structure of a biological molecule, comprising the steps of (a) contacting a polyrotaxane with the biological molecule to form a complex; (b) subjecting the complex to cryogenic electron microscopy; and (c) analyzing data collected from the cryogenic electron microscopy experiment. In some embodiments, the polyrotaxane is a crosslinked polyrotaxane.

In another aspect, the present invention provides a method of preparing a polyrotaxane that has an affinity binding group, comprising the steps of (a) mixing a linear axle molecule with a plurality of intermediate macrocyclic molecules to form a composite; (b) combining the composite with a compound having a capping group, whereby the capping group can be attached to each end of the linear axle molecule to form an intermediate polyrotaxane; and (c) converting the intermediate polyrotaxane to the polyrotaxane that has an affinity binding group.

The details of one or more embodiments of the invention are set forth in the accompanying description below. Other features, objects, and advantages of the invention will be apparent from the description and drawings, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
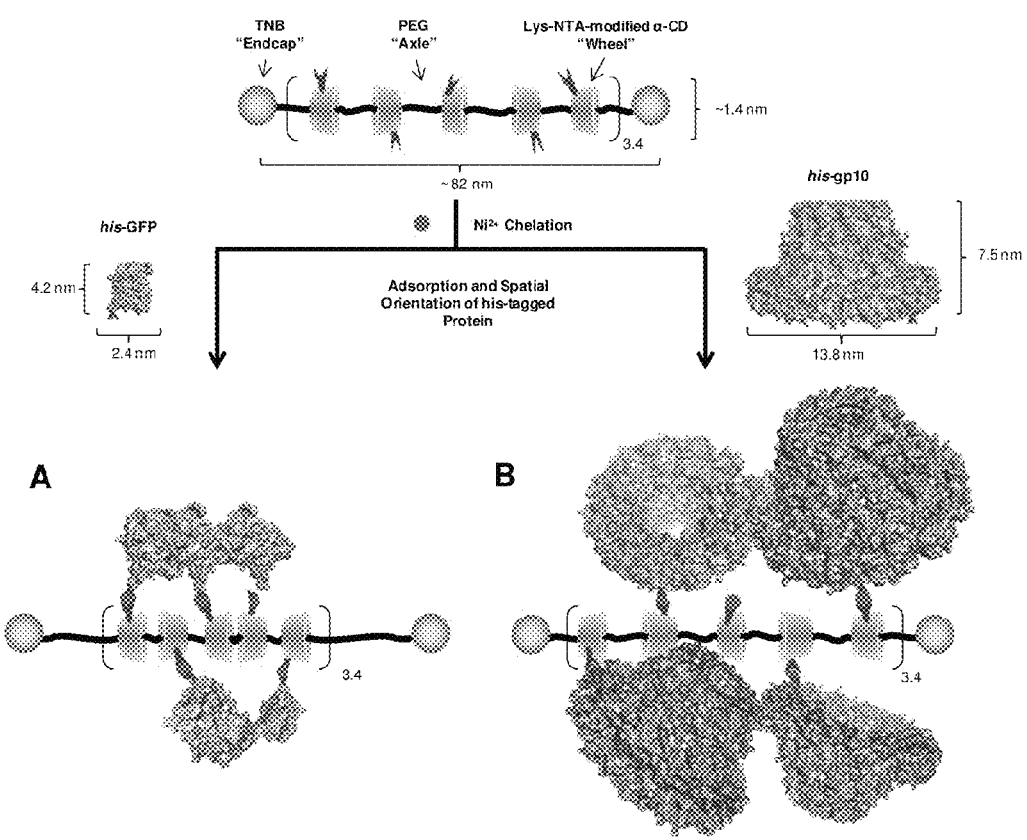
FIG. 1 depicts a conceptual diagram of his-tagged protein adsorption onto Lys-NTA-α-CD-polyrotaxane scaffolds.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

This invention is directed, in some embodiments, to a polyrotaxane that includes a plurality of macrocyclic molecules, a linear axle molecule that threads through the macrocyclic molecules, and a capping group at each end of the linear axle molecule, in which one or more of macrocyclic molecules comprise an affinity binding group and in which the macrocyclic molecules are laterally and rotationally mobile along the linear axle molecule.

In some embodiments, the invention is directed to a crosslinked polyrotaxane comprising two or more polyrotaxanes, wherein said polyrotaxanes each comprise a plurality of macrocyclic molecules and a linear axle molecule threading through the macrocyclic molecules, wherein one or more of the macrocyclic molecules comprise an affinity binding group and are laterally and rotationally mobile along the linear axle molecule, and wherein the linear axle molecule is crosslinked with another linear molecule. In some embodiments, the linear axle molecule is crosslinked with another linear molecule by a covalent bond or a non-covalent bond.

In some embodiments, the affinity binding group can be a metal chelate that can have a chelating agent moiety and a metal ion. In certain embodiments, the chelating agent moiety can be a polycarboxylic acid. In other embodiments, the chelating agent moiety can be nitrilotriacetic acid, tris (nitrilotriacetic acid), N$^1$,N$^4$,N$^8$-tris(nitrilotriacetic acid)-1,4,8,11-tetraazocyclotetradecane, or iminodiacetic acid. In some embodiments, the chelating agent moiety can be nitrilotriacetic acid.

In some embodiments, the metal ion can be Cu$^{2+}$, Ni$^{2+}$, Co$^{2+}$, Ca$^{2+}$, Mg$^{2+}$, Cd$^{2+}$, Gd$^{2+}$, Ru$^{2+}$, or Fe$^{2+}$. In other embodiments, the metal ion can be Co$^{2+}$, Cu$^{2+}$, or Ni$^{2+}$. In certain embodiments, the metal ion can be Ni$^{2+}$.

In some embodiments, the affinity binding group can be selected from the group consisting of antibodies, proteins, nucleotides, peptides, carbohydrates, drug leads, and analogs thereof. In other embodiments, the affinity binding group can be Protein A, Fab fragment, ubiquitin, aptamer, glutathione, glucosaminoglycan, chitin, amylase, or analogs thereof.

In some embodiments, macrocyclic molecules can be a modified cyclodextrin. In other embodiments, the macrocyclic molecules can be a modified α-cyclodextrin or β-Cyclodextrin. In certain embodiments, the macrocyclic molecules can be lysine-N$_α$,N$_α$-di(carboxylmethyl)-α-cyclodextrin. In some embodiments, the macrocyclic molecules can be a modified calixarene, resorcarene, or cucurbituril. In other embodiments, the macrocyclic molecules can be a modified calixarene.

In some embodiments, the linear axle molecule can be a polymer. In some embodiments, the linear axle molecule can be poly(ethylene glycol) or poly(propylene glycol). In certain embodiments, the linear axle molecule can be poly(ethylene glycol). In some embodiments, the linear axle molecule can be poly(ethylene glycol)-poly(propylene glycol)-poly(ethylene glycol) copolymer.

In some embodiments, the polymer can have an average molecular weight of from about 1 kDa to about 80 kDa. In other embodiments, the polymer can have an average molecular weight of about 5 kDa to about 20 kDa.

In some embodiments, the number of macrocyclic molecules can be from about 10 to about 900. In other embodiments, the number of macrocyclic molecules can be from about 10 to about 300. In certain embodiments, the number of macrocyclic molecules can be from about 15 to about 20.

In some embodiments, the capping group can be substituted phenyl or a steroid derivative. In some embodiments, the capping group can be substituted phenyl. In other embodiments, the capping group can be 2,4,6-trinitrophenyl.

In some embodiments, the macrocyclic molecules can be any cyclic molecules known in the art that allow a linear axle molecule to pass through the structural cavities of the macrocyclic molecules to form an interlocked molecule.

In some embodiments, a "macrocyclic molecule" can be a cyclic macromolecule or a macromolecular cyclic portion of a molecule. In other embodiments, a macrocyclic molecule can also refer to a macrocyclic compound. The macrocyclic molecule can be a porphyrin or an analog or derivative thereof. The macrocyclic molecule can be a polyether macrocycle, an analog or derivative, or a combination thereof, for example, a crown ether (e.g., benzo[24]crown-8). The macrocyclic molecule can be a calixarene or heterocalixarene, or an analog or derivative or a combination thereof. The macrocyclic molecule can be a cyclic oligosaccharide, for example, cyclodextrin (CD). In some embodiments, the "cyclodextrin" can be composed of glucose monomers coupled together to form a conical, hollow molecule with a cavity. The cyclodextrin in the present invention can be any suitable cyclodextrins, including alpha-, beta-, and gamma-cyclodextrins, and their combinations, analogs, and derivatives. The cyclodextrin can be either natural or modified, for example, modified with a chelating agent moiety or attached to other affinity binding groups.

The number of macrocyclic molecules can be from about 10 to about 900, or from about 7 to about 700, or from about 5 to about 600, or from about 2 to about 450. The number of macrocyclic molecules can be from about 20 to about 900, or from about 20 to about 700, or from about 20 to about 600, or about 20 to about 450. In some embodiments, the number of macrocyclic molecules can be from about 10 to about 300, or from about 10 to about 100. In other embodiments, the number of macrocyclic molecules can be from about 10 to 50. In certain embodiments, the number of macrocyclic molecules can be from about 15 to about 20.

In some embodiments, a "chelating agent" or "chelating agent moiety" refers to any polydentate ligand which is capable of coordinating a metal ion, either directly or after removal of protective groups. Thus, the polydentate ligand can form several bonds to a single metal ion. The chelating agent can be ethylenedinitrilotetraacetic acid (EDTA), diethylenetrinitrilopentaacetic acid (DTPA), diaminocyclohexanetetraacetic acid (DCTA), nitrilotris(methylene)triphosphonic acid (NTTA), 2-aminoethanethiol, thiobis(ethylenenitrilo)tetraacetic acid (TEDTA), $N^2$-acetamidoimino-diacetic acid (ADA), iminodiacetic acid (IDA), hydroxamic acid, carboxymethylated aspartate (CMA) and nitrilotriacetic acid (NTA), tris(nitrilotriacetic acid), $N^1,N^4,N^8$-tris(nitrilotriacetic acid)-1,4,8,11-tetraazocyclotetradecane, or analogs or homologs thereof. In some embodiments, the chelating agent is a polycarboxylic acid. In other embodiments, the chelating agent is nitrilotriacetic acid, tris(nitrilotriacetic acid), $N^1,N^4,N^8$-tris(nitrilotriacetic acid)-1,4,8,11-tetraazocyclotetradecane, or iminodiacetic acid. In some embodiments, the chelating agent is nitrilotriacetic acid. Thus, in some embodiments, the macrocyclic molecules of the present invention can be lysine-$N_\alpha,N_\alpha$-di(carboxylmethyl)-α-cyclodextrins.

In some embodiments, the "metal chelate" refers to a metal-ligand complex, and it is to be understood that the metal chelate can eventually be coordinated to a biological molecule.

In some embodiments, an "affinity binding group" refers to a group which interacts with molecules that can bind to it. The interaction can be selective and reversible. Examples of the affinity binding groups that can be employed in the practice of the present invention can be antibodies, antibody fragments, aptamers, proteins having an affinity for antibodies, Fc regions and/or Fab regions such as Protein G, Protein A, Protein A/G, and Protein L; chelated metals such as metal-NTA chelate (e.g., Nickel NTA, Copper NTA, Iron NTA, Cobalt NTA, Zinc NTA), metal-IDA chelate (e.g., Nickel IDA, Copper IDA, Iron IDA, Cobalt IDA) and metal-CMA (carboxymethylated aspartate) chelate (e.g., Nickel CMA, Copper CMA, Iron CMA, Cobalt CMA, Zinc CMA), nucleotides, oligonucleotides, polynucleotides and their analogs (e.g., ATP), lectin, heparin, avidin (Neutravidin, streptavidin), or a peptide or peptide analog (e.g., that binds to a protease or other enzyme that acts upon polypeptides or has a specific interaction with an affinity capture molecule or drug derivative). In some embodiments, the affinity binding group can be antibodies, proteins, nucleotides, peptides, carbohydrates, drug leads, or analogs thereof. In other embodiments, the affinity binding group can be Protein A, to Fab fragment, ubiquitin, SNAP tag, aptamer, glutathione, glucosaminoglycan, chitin, amylase, or analogs thereof. In some embodiments, the affinity binding group can be aptamers. In other embodiments, the affinity binding group can be antibodies. In certain embodiments, the affinity binding group can be a protein.

In some embodiments, the linear axle molecule of the present invention can be any linear compounds. The linear axle molecule can be a long-chain carbon molecule, optionally substituted with nitrogen atoms or oxygen atoms. In some embodiments, the linear axle molecule can also refer to a linear axle compound. In some embodiments, the linear axle molecule can be a polymer. The polymer can be a homopolymer. In some embodiments, a "homopolymer" is a polymer where only one type of monomers is used. Examples of homopolymers include, but are not limited to, polyvinyl alcohol, poly(meth)acrylic acid, polyacrylamide, poly(ethylene oxide), poly(propylene oxide), poly(ethylene glycol), polyisoprene, poly(propylene glycol), poly(vinyl methyl ether), polyethylene, polypropylene, polyisobutylene, polybutadiene, polyureas, polysulfides, polydimethylsiloxane. In some embodiments, the linear molecule may be selected from the group consisting of poly(ethylene glycol), poly(propylene glycol), polydimethylsiloxane, polyethylene, and polypropylene. In certain embodiments, the linear molecule can be poly(ethylene glycol) and poly(propylene glycol) copolymer. In other embodiments, the linear molecule can be poly(ethylene glycol) (PEG). In some embodiments, the linear axle molecule can be bifunctional PEG's, for example, a bis-maleimide PEG or a bis-biotin PEG. In other embodiments, the linear axle molecule can be multi-armed PEG's, e.g., 4-armed-PEG-MAL or 8-armed-PEG-MAL. In some embodiments, the linear axle molecule is a combination of bifunctional PEG's and multi-armed PEG's.

In some embodiments, the linear axle molecule can be a copolymer. A "copolymer" can be called a "heteropolymer." In some embodiments, a copolymer refers to a polymer derived from two or more monomeric species. It can be a block copolymer, which includes two or more chemically distinct homopolymer blocks linked by covalent bonds. The block copolymer can be a diblock copolymer, a triblock copolymer, or a block copolymer with more than three distinct blocks. For example, it can be poly(ethylene glycol)-poly(propylene glycol)-poly(ethylene glycol) triblock copolymer. Poloxamers (Pluronics®) are another triblock copolymer which is composed of a central chain of poly(propylene oxide) (PPO) flanked by two chains of poly(ethylene oxide) (PEO).

In some embodiments, the average molecular weight of the linear molecule, such as a polymer, may range from about 1 kDa to about 80 kDa, or from about 1 kDa to about 60 kDa, or from about 5 kDa to about 80 kDa, or from about 5 kDa to about 60 kDa. In some embodiments, the average molecular weight of the polymer can be from about 1 kDa to about 40 kDa, or from about 1 kDa to about 30 kDa, or from about 5 kDa to about 40 kDa, or from about 5 kDa to about 30 kDa, or from about 5 kDa to about 20 kDa. In some embodiments, the average molecular weight of the polymer may also range from about 1 kDa to about 10 kDa. In other embodiments, the average molecular weight of the polymer may range from about 20 kDa to about 30 kDa.

It is another aspect of the present invention that the polyrotaxane of the invention can be crosslinked to form crosslinked polyrotaxane network materials. The crosslinked polyrotaxane network materials may expedite the isolation of affinity tagged biological molecules, e.g., proteins, for cryoelectron microscopy analysis.

The linear axle molecules that can be used for production of the network structures include, but are not limited to, bifunctional PEG's, multi-armed PEG's, and the combination thereof. Exemplified linear homobifunctional and branched PEG derivatives are provided below.

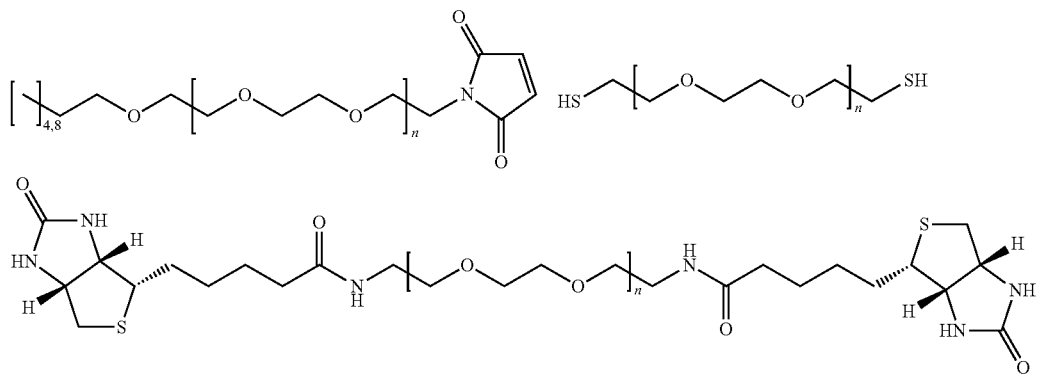

In some embodiments, the "average molecular weight" can refer to the weight average molecular weight (Mw) that can be calculated by Mw=$\Sigma N_i M_i^2 / \Sigma N_i M_i$ where $N_i$ is the number of molecules of molecular weight $M_i$.

In some embodiments, the macrocyclic molecules and the linear molecule may be connected by covalent bonds, or non-covalent interaction, or a combination thereof. When the macrocyclic molecules are not connected to the linear molecule, the macrocyclic molecules are free to move laterally or rotationally along the linear molecule. The macrocyclic molecule may rotate 360 degrees around the linear molecule. In the case of macrocyclic molecules being attached with an affinity binding group (e.g., a metal chelate), the affinity binding group may remain in different orientations around the linear molecule.

In some embodiments, to avoid dethreading of a macrocyclic molecule, a bulky group is normally attached to each end of the linear axle molecules, like a stopper. The bulky group to cap each end of the linear axle molecule can be dinitrophenyl groups, adamantane groups, trityl groups, other substituted benzenes (examples of the substituent may include, but are not limited to, alkyl, alkyloxy, hydroxy, halogen, cyano, sulfonyl, carboxyl, amino, phenyl and the like. The number of the substituents may be singular or plural); polycyclic aromatics which may be substituted (examples of the substituent may include, but are not limited to, alkyl, alkyloxy, hydroxy, halogen, cyano, sulfonyl, carboxyl, amino, phenyl and the like. The number of substituents may be singular or plural), and steroids. In some embodiments, the capping group can be a dinitrophenyl groups, adamantane groups, trityl groups, fluoresceins, and pyrenes. In some embodiments, the capping group can be substituted phenyl. In other embodiments, the capping group can be trinitrophenyl, for example, 2,4,6-trinitrophenyl.

Figure 8:
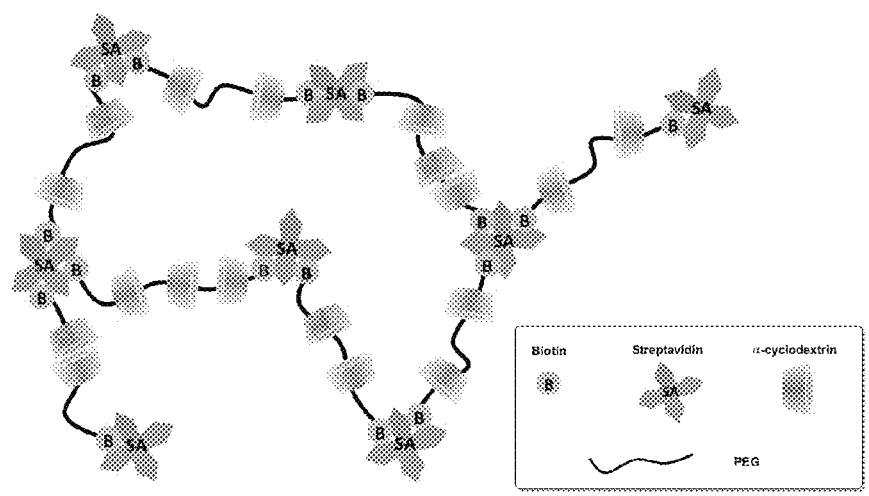
FIG. 8 illustrates a graphical representation of a Biotin-PEG-Biotin:SA hydrogel 2D structure.
Figure 9:
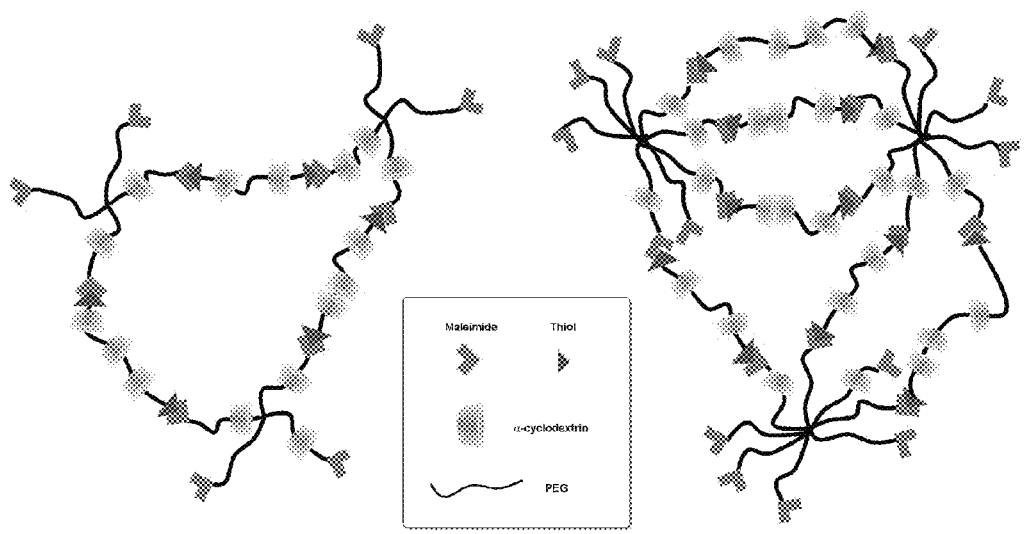
FIG. 9 illustrates a graphical representation of the 2D structure of a branched PEG polyrotaxane hydrogel network. Crosslinking density may be controlled by valency of the crosslinking agent and PEG molecular weight.

The bis-maleimide-, bis-thiol- and bis-biotin-PEG precursors can be used to produce pseudopolyrotaxanes via threading with a macrocyclic molecule, e.g., α-cyclodextrin (α-CD). The threaded pseudopolyrotaxanes can be crosslinked in the presence of unthreaded the macrocyclic molecules, e.g., α-CD, with 1,Ω-dithiopoly(ethylene glycol) in the case of bis-maleimido-poly(ethylene glycol):α-CD pseudopolyrotaxane, nanogold particles in the case of bis-thiol-poly(ethylene glycol):α-CD pseudopolyrotaxane or with streptavidin in the case of bis-biotinyl-poly(ethylene glycol):α-CD pseudopolyrotaxane. The resulting network structures to formed are depicted in FIGS. 8 and 9.

It is an important aspect of the present invention to prepare a biomolecule complex including a polyrotaxane of the present invention and a biological molecule.

The present invention, in some embodiments, provides a method of preparing a polyrotaxane that has an affinity binding group, comprising the steps of (a) mixing a linear axle molecule with a plurality of intermediate macrocyclic molecules to form a composite; (b) combining the composite with a compound having a capping group, whereby the capping group can be attached to each end of the linear axle molecule to form an intermediate polyrotaxane; and (c) converting the intermediate polyrotaxane to the polyrotaxane that has an affinity binding group.

In some embodiments, the affinity binding group can be a metal chelate that can have a chelating group moiety and a metal ion.

In some embodiments, step (c) comprises a step of reacting the intermediate polyrotaxane with a compound having the chelating agent moiety. In some embodiments, step (c) further comprises a step of removing a protective group.

In some embodiments, the chelating agent moiety can be a polycarboxylic acid. In other embodiments, the chelating agent moiety can be nitrilotriacetic acid, tris(nitrilotriacetic acid), $N^1,N^4,N^8$-tris(nitrilotriacetic acid)-1,4,8,11-tetraazocyclotetradecane, or iminodiacetic acid. In certain embodiments, the chelating agent moiety can be nitrilotriacetic acid.

In some embodiments, step (c) can further comprise a step of contacting a metal ion to form a metal chelate.

In some embodiments, step (c) can further comprise an activating agent. In certain embodiments, the activating agent can be carbonyldiimidazole.

In some embodiments, the affinity binding group can be selected from the group consisting of antibodies, proteins, nucleotides, peptides, carbohydrates, drug leads, and analogs thereof. In other embodiments, the affinity binding group can be Protein A, Fab fragment, ubiquitin, maltose, maltose binding protein, SNAP tag, aptamer, glutathione, glucosaminoglycan, chitin, amylose, or analogs thereof. In certain embodiments, the affinity binding group can be Protein A, Fab fragment, ubiquitin, aptamer, glutathione, glucosaminoglycan, chitin, amylose, or analogs thereof.

In some embodiments, step (c) can comprise a step of contacting the intermediate polyrotaxane with a compound that has an affinity binding group.

In some embodiments, the intermediate macrocyclic molecules can be a cyclodextrin. In other embodiments, the intermediate macrocyclic molecules can be an α-cyclodextrin or β-cyclodextrin. In some embodiments, the intermediate macrocyclic molecules can be a derivative or analog of a cyclodextrin. In certain embodiments, the intermediate macrocyclic molecules can be a calixarene.

In some embodiments, the linear axle molecule can be a polymer. In other embodiments, the linear axle molecule can be poly(ethylene glycol) or poly(propylene glycol). In certain embodiments, the linear axle molecule can be poly(ethylene glycol). In some embodiments, the linear axle molecule can be poly(ethylene glycol)-poly(propylene glycol)-poly(ethylene glycol) copolymer. In some embodiments, the linear axle molecule can be bifunctional PEG's, for example, a bis-maleimide PEG, bis-thiol PEG or a bis-biotin PEG. In other embodiments, the linear axle molecule can be multi-armed PEG's, e.g., 4-armed-PEG-MAL or 8-armed-PEG-MAL. In some embodiments, the linear axle molecule is a combination of bifunctional PEG's and multi-armed PEG's.

In some embodiments, the capping group can be substituted phenyl. In other embodiments, the capping group can be 2,4,6-trinitrophenyl.

In some embodiments, the terms "biological molecules" and "biomolecules" all refer to the commonly understood meanings of the terms, for example, as they apply to biological molecules such as proteins, lipids, polysaccharides, nucleic acids, as well as pharmacologically active small molecules, or complexes thereof. For example, multiple proteins may be bound to one another, or multiple proteins may be bound to multiple polysaccharides. In different contexts, the meaning of these terms will vary, as is appreciated by those of skill in the art. Unless otherwise specified, the meanings of these terms will be those generally accepted by those of skill in the art.

In some embodiments, the biological molecule may be any synthetic or naturally occurring biologically active therapeutic agents including those known in the art. Examples of suitable therapeutic agents include, but are not limited to, antibiotics, steroids, polynucleotides (e.g. genomic DNA, cDNA, mRNA and antisense oligonucleotides), plasmids, peptides, peptide fragments, small molecules (e.g. doxorubicin), natural products (e.g. Taxol, Amphotericin), and other biologically active macromolecules such as, for example, proteins and enzymes.

In some embodiments, the term "proteins" refers to any chain of amino acids, regardless of length or post-translational modification. Proteins can exist as monomers or multimers, comprising two or more assembled polypeptide chains, fragments of proteins, polypeptides, oligopeptides, or peptides.

In some embodiments, the macrocyclic molecules of a polyrotaxane may have an affinity binding group such as a metal chelate. The metal ion in a metal chelate in general can be any metal ion capable of being chelated by a biological molecule. The metal ion includes, but is not limited to, $Cu^{2+}$, $Ni^{2+}$, $Co^{2+}$, $Ca^{2+}$, $Mg^{2+}$, $Cd^{2+}$, $Gd^{2+}$, $Ru^{2+}$, or $Fe^{2+}$. In some embodiments, the metal ion can be $Co^{2+}$, $Cu^{2+}$, or $Ni^{2+}$. In other embodiments, the metal ion can be $Ru^{2+}$, $Ni^{2+}$, or $Fe^{2+}$. In certain embodiments, the metal ion can be $Ni^{2+}$.

In some embodiments, the polyrotaxanes of the present invention may have an affinity binding group other than a metal chelate. For example, the affinity binding group can be antibodies, proteins, nucleotides, peptides, carbohydrates, drug leads, or analogs thereof. In other embodiments, the affinity binding group can be antibodies, proteins, or analogs thereof. In some embodiments, the affinity binding group can be carbohydrates, drug leads, or analogs thereof. In some embodiments, the affinity binding group can be Protein A, Fab fragment, ubiquitin, aptamer, glutathione, glucosaminoglycan, chitin, amylose or analogs thereof. In other embodiments, the affinity binding group can be Protein A, Fab fragment, aptamer, or analogs thereof. In certain embodiments, the affinity binding group can be ubiquitin, maltose, maltose binding protein, SNAP tag, glutathione, glucosaminoglycan, chitin, amylase, or analogs thereof. In some embodiments, the affinity binding group can be ubiquitin, glutathione, glucosaminoglycan, chitin, amylase, or analogs thereof. In some embodiments, the affinity binding group can be glutathione or analogs thereof. In certain embodiments, the affinity binding group can be chitin or analogs thereof.

It is an important aspect of the invention that a biological molecule can be bound to, or captured by, the affinity binding group of a polyrotaxane to form a biomolecule complex. In some embodiments, the term "binding" can refer to non-covalent interactions of an affinity binding group with a biological molecule. These non-covalent interactions include, inter alia, hydrophobic, hydrophilic, dipole-dipole, pi-stacking, hydrogen bonding, electrostatic associations, Lewis acid-base interactions, or a combination thereof. In some embodiments, the non-covalent interactions can be independent from one another.

Various sizes of biological molecules can be captured by the affinity binding groups of a polyrotaxane of the invention, for example, the metal chelate of the polyrotaxane. The molecular weight of the biological molecule can range from about 20 kDa to about 10,000 kDa, or from about 20 kDa to about 5,000 kDa, or from about 20 kDa to about 1,000 kDa, or from about 25 kDa to about 700 kDa, or from about 25 kDa to about 500 kDa. The biological molecule may have a molecular weight of from about 20 kDa to about 100 kDa or from about to 40 kDa to about 100 kDa, or from about 100 kDa to about 200 kDa. The biological molecule may have a molecular weight of from about 200 kDa to about 250 kDa or from about 250 kDa to about 400 kDa. The biological molecule may have a molecular weight of from about 300 kDa to about 500 kDa.

In some embodiments, for a relatively small biological molecule, for example, $his_6$-GFP, which has a molecular weight of about 31 kDa, the number of the biological molecules and the number of macrocyclic molecules in a biomolecule complex can be in a ratio of about 1:1. The biological molecules on the surface can be densely packed along the polyrotaxane, thus forming a thin layer of biological molecules surrounding the polyrotaxane. In some embodiments, the number of the biological molecules and the number of the macrocyclic molecules in a biomolecule complex can be in a ratio of about 1:2 or about 1:3. In other embodiments, the number of the biological molecules and the number of the macrocyclic molecules in a biomolecule complex can be in a ratio from about 1:1 to about 1:5. Comparatively, for a large biological molecule, for example, large protein assemblies, $his_6$-gp10 connector polypeptide which has a molecular weight of about 440 kDa, the macrocyclic molecules in a polyrotaxane may not all become bound to the biological molecule due to molecular crowding. It can be inferred that the biological molecules are in spatial proximity to one another. In some embodiments, the number of biological molecules and the number of macrocyclic molecules in a biomolecule complex may be in a ratio of about 1:2 or about 1:3. In some embodiments, the number of biological molecules and the number of macrocyclic molecules in a biomolecule complex may be in a ratio of from about 1:2 or about 1:5. In other embodiments, the number of biological molecules and macrocyclic molecules in a biomolecule complex can be in a ratio of about 1:1, when only a few number of macrocyclic molecules are present in the polyrotaxane. In any cases, the adsorbed biological molecule is presented in all possible orientations due to the dynamic mobility of the macrocyclic molecules to which they are linked.

The polyrotaxanes of the present invention may be synthesized in a variety of ways. For instance, a linear molecule and a macrocyclic molecule can be combined under a condition that is sufficient to form a composite, e.g., an interlocked molecule (in some embodiments, a composite can be called an "interlocked molecule" herein). The macrocyclic molecule may to contain a side chain, e.g., an affinity binding group, or may not have a side chain. The formation of the interlocked molecule can be achieved at 25° C. or at a temperature between 0° C. and 25° C., e.g., 5° C. In some embodiments, the formation of the interlocked molecule can be achieved at a temperature of from about 25° C. to about 60° C., e.g., about 45° C. Both the linear molecule and the macrocyclic molecule may be dissolved in an aqueous solution, in an organic solvent, or may be mixed in the solid state. The organic solvent for dissolving the linear molecule and the macrocyclic molecules can be tetrahydrofuran (THF), alcohol (e.g., methanol, ethanol, or propanol), DMF, DMSO, or other organic solvent known to one skilled in the art, or a combination thereof. In some embodiments, a solution of the linear molecule and the macrocyclic molecules can be stirred overnight to yield an interlocked molecule. In other embodiments, an interlocked molecule can be obtained by sonicating a solution of the linear molecule and the macrocyclic molecules at 25° C., or at a temperature between 0° C. and 25° C., or at a temperature of from about 25° C. to about 45° C., or at a temperature from about 45° C. to about 60° C. In some embodiments, grinding or compressing the solids together can also yield interlocked molecules.

In some embodiments, treatment of the interlocked molecule with a compound containing capping groups can give an interlocked molecule with the linear axle molecule being capped, thus forming an intermediate polyrotaxane. The capping group can be any bulky groups known in the art so as to prevent detachment of the macrocyclic molecules. The capping group can be bound to each end of the linear molecule by a chemical bond. For example, 2,4,6-trinitrobenzenesulfonic acid or sodium 2,4,6-trinitrobenzenesulfonate can readily react with a linear molecule that has an amino group at each end under a mild condition to afford an intermediate polyrotaxane, with a capping group at each end of the linear molecule.

In some embodiments, in the case of forming crosslinked polyrotaxane network materials, instead of being treated with a compound having a capping group, the interlocked molecule can be combined with a compound that is capable of crosslinking the linear axle molecules, thus forming an intermediate polyrotaxane network. For example, a linear molecule having a thiol group can crosslink with bis-maleimide PEG. As a result, the formed crosslinked intermediate polyrotaxane network can prevent unthreading of the macrocyclic molecule(s) from the linear molecule(s) in the polyrotaxane.

In some embodiments, the term "crosslink" refers to a bond that links one polymer chain to another polymer chain, including proteins or other biological molecules, by a covalent bond or a non-covalent bond.

In some embodiments, the resulting intermediate polyrotaxane can further be modified on its macrocyclic molecules under a condition that is sufficient to produce any derivatives of the intermediate polyrotaxane. For example, the intermediate polyrotaxane can be modified to form a chemical bond with an affinity binding group. The affinity binding group can be a cyclic group or a linear group, or a combination thereof. The intermediate polyrotaxane can be converted to a polyrotaxane having an affinity binding group by the chemistry known to those skilled in the art based on the nature of the affinity binding group. In some embodiments, more than one group, for example, two groups, or three groups, or more than three groups, may be incorporated on the macrocyclic molecules of the intermediate polyrotaxane.

In some embodiments, an intermediate polyrotaxane can be coupled with an affinity group or a compound containing an affinity group to afford a polyrotaxane of the invention. The coupling reaction may require the presence of a catalyst, or a promoter, or an activating agent. The coupling reaction may be conducted under a mild condition in an aqueous solution or an organic solvent that can dissolve the intermediate polyrotaxane and the compound containing an affinity group. The organic solvent can be DMF, DMSO, or THF, or other organic solvent known in the art that is capable of dissolving the coupling compounds. In some embodiments, the solvent can be a mixture of two or more different solvents. For example, a mixture of water and an alcohol (e.g., methanol or ethanol). The temperature for the coupling reaction can be 25° C. or from about 45° C. to about 60° C. In some cases, the temperature can be from about 60° C. to about 80° C. In other cases, the temperature can be from about 80° C. to about 100° C., or a temperature that is appropriate for the reaction to occur.

In some embodiments, the modification of the macrocyclic molecules can be conducted before introduction of capping groups at each end of the linear molecule. For example, the macrocyclic molecules may couple with affinity groups to form modified macrocyclic molecules. Thus, the modified macrocyclic molecules may form an interlocked molecule (or a composite) with a linear axle molecule, followed by attaching a capping group at each end of the linear molecule.

In some embodiments, the protected polyrotaxane is an intermediate polyrotaxane, which can be further treated to remove protective groups to provide a polyrotaxane of the invention. The protective groups can be removed under a condition known to those skilled in the art, for example, as exemplified in: *Protective Groups in Organic Synthesis,* 2nd Ed., Greene, et al. 1991, John Wiley and Sons, Inc., New York. For example, in the case of a t-butyl protected carboxylic acid compound, trifluoroacetic acid in methylene chloride at 20° C. can give an excellent yield of the unprotected carboxylic acid compound, which can further form a metal chelate with a metal ion.

In some embodiments, a biomolecule complex can be obtained by contacting a polyrotaxane of the present invention with a biological molecule. In some embodiments, a "biomolecule complex" can refer to a polyrotaxane of the invention attached, bound, or otherwise linked to its intended/target biological molecules through an affinity binding group. The polyrotaxane that has affinity towards biological molecules may form a biomolecule complex with the biological molecules through a non-covalent bond. For example, a metal chelate and a biological molecule can be complexed or coordinated with a metal ion.

In some embodiments, mixing a solution of a biological molecule with a polyrotaxane of the invention at 25° C. can lead to the formation of a biomolecule complex. In other embodiments, the formation of a biomolecule complex can be achieved at about 0° C. or at a temperature between 0° C. and 25° C. In certain embodiments, the temperature is below 0° C., for example, about −5° C. or about −10° C. The biological molecule can be present in water or an aqueous solution, e.g., in a buffer solution. The buffer solution for the biological molecule can be HEPES, HEPPS, TAPSO, MOPS, or TES. In some embodiments, the buffer solution is HEPES or HEPPS. In certain embodiments, the buffer solution is HEPES. The pH value required for the buffer solution can be from about 7.0 to about 8.0. In some embodiments, the to pH value of the buffer solution is from about 7.2 to about 7.8. In other embodiments, the pH value of the buffer solution is from about 7.3 to about 7.6. In certain embodiments, the pH value of the buffer solution is about 7.4. Upon formation of a biomolecule complex, the biological molecule becomes bound or adsorbed to the polyrotaxane.

In the cases that the affinity binding group can be a metal chelate, the biological molecule may be first complexed to a metal ion that can further bind an intermediate polyrotaxane containing a chelate agent moiety. In some embodiments, the intermediate polyrotaxane first can form a metal chelate with a metal ion that may be linked to a biological molecule subsequently.

In some embodiments, a metal chelate can be obtained by mixing an intermediate polyrotaxane containing a chelating agent moiety with a metal ion at a temperature sufficient to form a metal chelate. For example, at 0° C., or at 25° C., or at a temperature between 0° C. and 25° C., for example, at about 20° C. In some embodiments, a metal chelate may form at an elevated temperature, e.g., from about 45° C. to about 60° C., or from about 60° C. to about 80° C., or from about 80° C. to about 100° C. In the metal chelate, the ratio of metal ion content to the chelating agent can be from about 1:1 to about 1:3. In some embodiments, the ratio of metal ion content to the chelating agent can be about 1:1. For example, when a metal ion is $Ni^{2+}$ and the polyrotaxane is Lys-NTA-α-CD:PEG (10K), the ratio of the $Ni^{2+}$ content to Lys-NTA-α-CD is about 1:1.

In some embodiments, the metal chelate can be isolated and purified and then ready for the next reaction steps. In some embodiments, it is not necessary to isolate or purify the metal chelate from reaction mixtures. The metal chelate can be used upon formation.

In some embodiments, a biomolecule complex containing a metal chelate can be obtained by simply mixing the biological molecule, a metal ion, and an intermediate polyrotaxane under a condition sufficient to form the biomolecule complex. The temperature can be 0° C. or 25° C., or at a temperature between 0° C. and 25° C., for example, about 20° C. In some embodiments, the temperature can be below 0° C., for example, about −5° C. or about −10° C. The biological molecule can be in a buffer solution such as HEPES, HEPPS, TAPSO, MOPS, or TES and the pH value of the solution can range from about 7.0 to about 8.0. In some embodiments, the buffer solution is HEPES or HEPPS and the pH value of the solution can be from about 7.4 to about 7.6. In certain embodiments, the buffer solution is HEPES with a pH value of 7.4.

To expedite the isolation of affinity tagged biological molecules, e.g., protein, for cryoelectron microscopy analysis, a family of crosslinked polyrotaxane network structures or materials can be used. These structures are suitable for production of thin membranes on TEM grids for specific capture of affinity tagged biological molecules. Modification of the macrocyclic molecules of this network enables the specific capture and presentation of affinity tagged biological molecules, e.g., proteins, in multiple orientations within a thin membrane on a TEM grid support for single particle reconstruction analysis.

In some embodiments, the crosslinked polyrotaxane network structures can be cast into thin membrane films using two different methods. In the first case, the solution-formed networks were filtered through a TEM grid to form a composite film that was mechanically stable and approximately 200 nm in thickness. In the second case, TEM grids were used as the reactive zone of an interfacial polymerization wherein one component was dissolved in a water miscible solvent (e.g., DMSO, DMF, MeCN, etc) that was introduced in between the grid bars of the TEM grid. The second component of the network was then layered onto the TEM grid as an aqueous solution such that reaction between the two components in the diffusion layer between the $H_2O$ and organic phases produced a network structure that deposited onto the TEM grid.

It is another aspect of the present invention to provide a method of characterizing or determining a three-dimensional structure of a biological molecule. In some embodiments, the method includes the steps of (a) contacting a polyrotaxane with the biological molecule to form a complex; (b) subjecting the complex to cryogenic electron microscopy; and (c) analyzing data collected from the cryogenic electron microscopy experiment.

In some embodiments, the polyrotaxane comprises a plurality of macrocyclic molecules, a linear axle molecule that can thread through the macrocyclic molecules, and a capping group at each end of the linear axle molecule, in which one or more of the macrocyclic molecules comprise an affinity binding group and in which the macrocyclic molecules can be laterally and rotationally mobile along the linear axle molecule.

In some embodiments, the polyrotaxane is a crosslinked polyrotaxane, wherein the crosslinked polyrotaxane includes two or more polyrotaxanes, wherein said polyrotaxanes each can comprise a plurality of macrocyclic molecules and a linear axle molecule threading through the macrocyclic molecules, wherein one or more of the macrocyclic molecules comprising an affinity binding group can be laterally and rotationally mobile along the linear axle molecule, and wherein the linear axle molecule can be crosslinked with another linear molecule. In some embodiments, the linear axle molecule can be crosslinked with another linear molecule by a covalent bond or a noncovalent bond. In some embodiments, the crosslinked polyrotaxane can be in a form of a thin membrane for specific capture of affinity tagged biological molecules. In other embodiments, the thin membrane can be deposited on TEM grids.

In some embodiments, the affinity binding group can be a metal chelate that has a chelating agent moiety and a metal ion. In some embodiments, the chelating agent moiety can be a polycarboxylic acid. In other embodiments, the chelating agent moiety can be nitrilotriacetic acid, tris(nitrilotriacetic acid), $N^1,N^4,N^8$-tris(nitrilotriacetic acid)-1,4,8,11-tetraazocyclotetradecane, or iminodiacetic acid. In some embodiments, the chelating agent moiety can be nitrilotriacetic acid or iminodiacetic acid. In certain embodiments, the chelating agent moiety can be nitrilotriacetic acid.

In some embodiments, the metal ion can be $Cu^{2+}$, $Ni^{2+}$, $Co^{2+}$, $Ca^{2+}$, $Mg^{2+}$, $Cd^{2+}$, $Gd^{2+}$, $Ru^{2+}$, or $Fe^{2+}$. In other embodiments, the metal ion can be $Co^{2+}$, $Cu^{2+}$, or $Ni^{2+}$. In certain embodiments, the metal ion can be $Ni^{2+}$.

In some embodiments, the affinity binding group can be selected from the group consisting of antibodies, proteins, nucleotides, peptides, carbohydrates, drug leads, and analogs to thereof. In other embodiments, the affinity binding group can be Protein A, Fab fragment, ubiquitin, peptide tags, protein tags, SNAP tags, aptamer, glutathione, glucosaminoglycan, chitin, amylose or analogs thereof. In other embodiments, the affinity binding group can be Protein A, Fab fragment, ubiquitin, aptamer, glutathione, glucosaminoglycan, chitin, amylose or analogs thereof.

In some embodiments, the macrocyclic molecules can be a modified cyclodextrin. In some embodiments, the macrocyclic molecules can be a modified α-cyclodextrin or a modified β-cyclodextrin. In certain embodiments, the macrocyclic molecules can be lysine-$N_\alpha,N_\alpha$-di(carboxylmethyl)-α-cyclodextrin. In some embodiments, the macrocyclic molecules can be a modified calixarene, resorcarene, or cucurbituril. In some embodiments, the macrocyclic molecules can be a modified calixarene.

In some embodiments, the linear axle molecule can be a polymer. In some embodiments, the linear axle molecule can be poly(ethylene glycol) or poly(propylene glycol). In other embodiments, the linear axle molecule can be poly(ethylene glycol). In certain embodiments, the linear axle molecule can be poly(ethylene glycol)-poly(propylene glycol)-poly(ethylene glycol) copolymer.

In some embodiments, the polymer can have an average molecular weight of from about 1 kDa to about 80 kDa.

In some embodiments, the biological molecule can have a molecular weight of from about 20 kDa to about 10,000 kDa. In other embodiments, the biological molecule can have a molecular weight of from about 20 kDa to about 5000 kDa. In certain embodiments, the biological molecule can have a molecular weight of from about 20 kDa to about 1000 kDa. In some embodiments, the biological molecule can have a molecular weight of from about 25 kDa to about 500 kDa.

In some embodiments, the biological molecule can be a protein, a lipid, a nucleic acid, an oligosaccharide, or a complex thereof. In certain embodiments, the biological molecule can be a protein or a complex thereof.

In some embodiments, the number of the biological molecule and the number of macrocyclic molecules in a biomolecule complex can have a ratio of from about 1:6 to about 1:1. In other embodiments, the number of the biological molecule and the number of macrocyclic molecules in a biomolecule complex can have a ratio of from about 1:4 to about 1:1. In some embodiments, the number of the biological molecule and the number of macrocyclic molecules in a biomolecule complex can have a ratio of about 1:1.

The biomolecule complex can be characterized by a variety of methods as known in the art. For example, the formation of the biomolecule complex can be visualized by Fluorescence Microscopy, Atomic Force Microscopy, and Cryogenic Electron Microscopy (Cryo-EM). For example, Cryo-EM imaging of a biomolecule complex can reveal the morphologies of the biomolecule complex as exemplified in Example 6.

A biological molecule can be restored followed by decomplexation of a biomolecule complex. For example, treatment of the biomolecule complex with a decomplexation compound, for example, imidazole, can restore the biological compound, which confirms the reversible complexation of the biological molecule with the metal chelate of the invention.

A biological molecule in complex with the polyrotaxane of the invention provides an opportunity to elucidate the structural information of the individual biological molecule. It is an important aspect of the present invention that the polyrotaxane can be used for characterization and determination of the three-dimensional structures of biological molecules, such as proteins.

The polyrotaxane of the invention possesses uniquely advantageous properties resulting from the non-covalent interactions between the linear axle molecule and the threaded macrocyclic molecules, for example, the free lateral and rotational mobility of the threaded macrocyclic molecules. Upon formation of a biomolecule complex with a polyrotaxane of the invention, the biological molecules in the complex are bound or attached to the macrocyclic molecules of the polyrotaxane. Due to the mobility of the macrocyclic molecules, the biological molecules can be in different orientations in the complex. Thus, the three-dimensional structures of an individual biological molecule in a biomolecule complex can be characterized or determined by methods known in the art. One method involves the use of Cryogenic Electron Microscopy (Cryo-EM) that can capture images of biomolecule complexes. The obtained Cryo-EM images can be then analyzed by Single Particle Analysis techniques.

When a biomolecule complex is subjected to Transmission Electron Microscopy, for example, Cryogenic Electron Microscopy (Cryo-EM), each Cryo-EM image can reveal all three-dimensional orientations of the captured biological molecule in a biomolecule complex. This also can accelerate and facilitate Single Particle Analysis (SPA) by Cryo-EM. The captured biological molecules in a biomolecule complex stay close to each other on a spatially well-defined linear molecule scaffold. As a result, data collection can be expedited by a relatively high concentration of the biological molecule at the polyrotaxane surface rather than the biological molecule being randomly distributed in solution. Moreover, the polyrotaxane offers a constant diameter template; and the rod-like polyrotaxane morphology should suppress information loss due to biological molecules overlap and secondary scattering events in projection EM images that is likely in a conventional polymer modification approach.

The polyrotaxane of the invention provides an efficient means for imaging the three-dimensional structures of the biological molecule in complex with the polyrotaxane of the invention and processing the images, therefore, allowing to obtain more detailed information regarding the structure of a biological molecule more quickly and more accurately than previously possible. This improvement in characterization and determination involves (1) enabling the capture of biological molecules of substantially different size and facilitating their imaging via AFM, Cryo-TEM, and negative stain TEM; (2) increasing the concentration of the biological molecules in the field of view at the magnification required to image the nanoscale targets; (3) revealing projection images of the biological molecule structure in all possible three-dimensional orientation; and (4) reducing both the amount of purified biological molecules, e.g., protein, necessary for SPA and the time required for acquisition of the large particle counts needed for high resolution analysis.

The polyrotaxane of the invention provides an efficient method for imaging the three-dimensional structures of the biological molecule in the complex with the polyrotaxane of the invention. In some embodiments, the method of the invention can include the step of comparing the obtained three-dimensional structure of the biological molecule and the known three-dimensional structures of biological molecules in the art. In other embodiments, the method can include the step of analyzing and providing structural information about unknown biological molecules. In the case that the concentration of a biological molecule may be low, the polyrotaxane of the invention may include an affinity binding group that recognizes or has specificity for a certain biological molecule, therefore, specifically binding to and identifying the biological molecule. The biological molecule captured by the polyrotaxane of the invention due to the formation of the polyrotaxane and biological molecule complex can be characterized and determined. In some embodiments, the method of the invention can be useful to aid in screening and development of diagnostic and therapeutic biological molecules or their structural analogs or fragments. A biological molecule containing a polyrotaxane of the present invention can be restored followed by decomplexation of a biomolecule complex. In some embodiments, the biomolecule complex can be used as a carrier to deliver any biological molecule to effect a therapeutic benefit.

It will be appreciated by persons skilled in the art that the present invention is not limited by what has been particularly shown and described herein above. Rather the scope of the present invention includes both combinations and subcombinations of the various features described hereinabove as well as variations and modifications which would occur to persons skilled in the art upon reading the specification and which are not in the prior art.

The invention will be further illustrated with reference to the following illustrative examples, which are not intended to limit the scope of the invention in any manner.

EXAMPLES

Example 1. Synthesis of Lys-NTA-α-CD:PEG(10K) Polyrotaxane (4) (FIG. 10)

Polyrotaxanes of the present invention that are capable of forming a complex with a biological molecule can be prepared as shown in the following examples. In some to embodiments, for the convenience of descriptions in the experiments, intermediate polyrotaxanes that do not contain an affinity binding group may be called polyrotaxane as indicated in the following examples.

Figure 10:
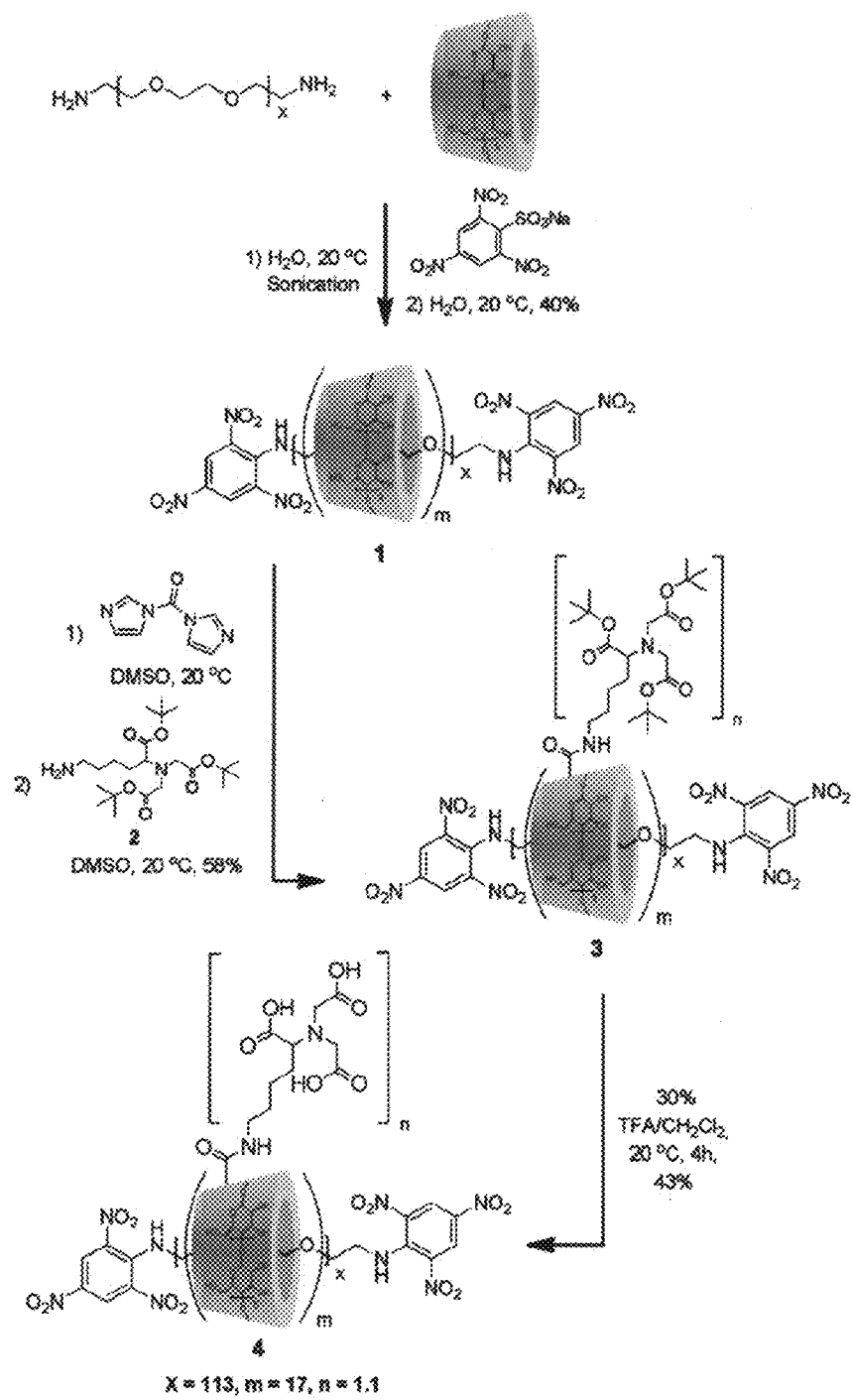
FIG. 10 depicts Scheme 1 for synthesis of Lys-NTA-α-CD:PEG10K polyrotaxane.

In this example, Lys-NTA-α-CD:PEG(10K) polyrotaxane (4) was obtained in satisfactory yield by post-modification of TNB-capped-α-CD-PEG10K polyrotaxane (1) via carbonyldiimidazole activation and coupling with t-butyl-protected Lys-NTA (2) (Scheme 1) (FIG. 10). After TFA deprotection, the observed molecular weight of Compound 4 was 31,900 g/mol by GPC analysis. $^1$H-NMR spectra of 1 and 3 revealed the presence of 17 α-CD units and 19 NTA substituents, indicating a 15% threading efficiency and an NTA:α-CD ratio of approximately 1:1.

Materials

Poly(ethylene glycol) ($M_n$=10,000, PEG10K) and 2,4,6-trinitrobenzenesulfonic acid (1.0 M in $H_2O$) were purchased from Aldrich. Sodium 2,4,6-trinitrobenzenesulfonate (TNBS) was obtained by neutralization of 2,4,6-trinitrobenzenesulfonic acid solution with $NaHCO_3$. α-Cyclodextrin (α-CD) was purchased from Tokyo Kasei Inc. Other solvents and reagents were purchased from Aldrich and used without purification. t-Butoxy $N^\alpha,N^\alpha$-bis(t-butoxycarboethoxy)lysinate (Boc-Lys-NTA) was synthesized as described by Hyun et. al. (*J. Am. Chem. Soc.* 2010, 132, 17053). Dimethyl sulfoxide (DMSO) was distilled from $CaH_2$, dichloromethane (DCM) was distilled from $CaH_2$, and tetrahydrofuran (THF) was distilled from sodium benzophenone ketyl. DMSO-$d_6$ was used as solvent for $^1$H-NMR experiments (300 MHz) and the residual solvent peak used as internal standard.

Example 1-A. Synthesis and Characterization of PEG10K-bis-amine

Scheme 2. Synthesis of PEG-10K-bis-amine

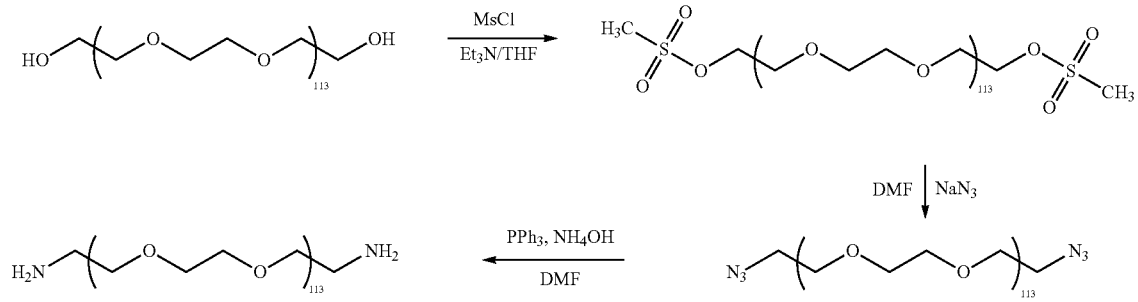

PEG10K-bis-amine ($H_2N$-PEG10K-$NH_2$) was synthesized in three steps following a modified procedure that has been previously reported (Singh, et al. *Bioconjug. Chem.* 2008, 19, 2239, and Susumu, et al. *Nat. Protoc.* 2009, 4, 424). In the first step, PEG-10K (50 g, 5 mmol) was dissolved in toluene (300 mL) and dried by rotary evaporation three times followed by to drying under a ~50 μm vacuum at 20° C. overnight. Next, THF (250 mL) was added and the PEG allowed to dissolve, followed by addition of methansulfonyl chloride (0.928 mL, 11.5 mmol). Then, triethylamine (1.8 mL, 12.5 mmol) was added dropwise over a period of 30 min and the solution was stirred for 24 h at 20° C. Next, the solution was filtered, the volume reduced by rotary evaporation, and the polymer product was purified by precipitation into diethyl ether (1 L) three times. After filtration and drying overnight under a ~50 μm vacuum at 20° C., the dimesylate was obtained as a white powder (43 g, 86% yield).

The residue was dissolved in 200 mL DMF before addition of $NaN_3$ (0.89 g, 13.6 mmol). The solution was heated at 80° C. for 4 d. The solvent was evaporated and the residue dissolved in minimal DCM (50 mL), filtered, and precipitated against diethyl ether (1 L) three times to give the diazide as a tan powder after filtration and drying overnight under a ~50 μm vacuum at 20° C. (34 g, 78% yield).

Finally, $N_3$—PEG10K—$N_3$ (20 g, 2 mmol) was dissolved in 150 mL DMF and $PPh_3$ (2.1 g, 8 mmol) added before stirring the solution for 1 h. Then, an aqueous $NH_4OH$ solution (20 mL, 35%) was added and the mixture stirred for 3 d. After solvent evaporation, the residue was dissolved in DCM (50 mL), filtered, and precipitated into diethyl ether (1 L) three times to give the diamine as a tan powder after filtration and drying under a ~50 μm vacuum at 20° C. overnight (17 g, 87% yield).

Example 1-B. Preparation of Pseudopolyrotaxane and Synthesis of PEG-10K Polyrotaxane α-CD (2.0 g, 2 mmol) was fully dissolved in 15 mL of deionized $H_2O$ before addition of PEG10K-bis-amine (177 mg). The mixture was sonicated for 30 min at 20° C. and the resulting white gel-like substance stored at 20° C. for 12 h. Sodium 2,4,6-trinitrobenznesulfonate (0.3 g, 1 mmol) and $NaHCO_3$ (100 mg, 1.2 mmol) were then added as an aqueous slurry and stirred at 20° C. for 12 h. The reaction mixture was washed sequentially with water and THF three times each before dialyzing the product (molecular weight cut-off 6,000-8,000) against DMSO for 3 d, then water for 3 d. The retained dialysate was then lyophilized to give Polyrotaxane 1 as a yellow powder (870 mg, 40% yield) (Loethen, et al. *Biomacromolecules*, 2006, 7, 2501; Ohya, et al. *Biomacromolecules*, 2009, 10, 2261; and Yang et al. *Macromolecules*, 2009, 42, 3856).

Example 1-C. Synthesis of NTA-Modified PEG-10K Polyrotaxane (4)

Polyrotaxane 1 (200 mg, 7.42 μmol) was dried in a 100 mL round bottom flask at 40° C. under vacuum for 48 h before adding dry DMSO (20 mL) and stirring until the material dissolved. N,N'-Carbonyldiimidazole (CDI, 1.328 g, 8.19 mmol) was added to the polyrotaxane solution and the reaction allowed to proceed for 24 h at 20° C. under a $N_2$ atmosphere. The reaction mixture was precipitated using a mixed ethereal solution (160 mL dry $Et_2O$ and 50 mL dry THF). The precipitate was added to NTA intermediate 2 (0.485 g, 1.13 mmol) in 10 mL dry DMSO and triethylamine (0.181 mL, 1.30 mmol) and the reaction stirred for 24 h at 20° C. under $N_2$. The product was dialyzed (molecular weight cut-off 2,000) against DCM for 1 d before removing the remaining DMSO under vacuum at 63° C. The residue was purified by Sephadex LH-20 column chromatography using 4:6 MeOH:$CH_2Cl_2$ as eluent. The isolated fractions of Polyrotaxane 3 were combined and evaporated to dryness (150 mg, 4.27 μmol, 58% yield).

To the purified sample of 3 was added 30% TFA in DCM with stirring for 6 h to deprotect the NTA t-butyl esters. The resulting solution was evaporated and the residue purified by Sephadex G-25 gel filtration chromatography using water as eluent. Polyrotaxane 4 recovered by lyophilization (103 mg, 3.23 μmol, 43%).

Example 2. His-Tagged Protein Adsorption onto Lys-NTA-α-CD-polyrotaxane Scaffolds FIG. 1 is a concept diagram of his-tagged protein adsorption onto Lys-NTA-α-cyclodextrin-polyrotaxane scaffolds. Polyrotaxanes bearing multiple laterally- and rotationally-mobile-Lys-NTA-α-CD's facilitate adsorption of his-tagged proteins. The relatively small protein, $his_6$-GFP (31 kDa), yields a complex with a high degree of α-cyclodextrin (CD) mobility, enabling favorable CD-CD and GFP-GFP interactions. His-GFP is referred to his-tagged GFP (e.g., a short stretched of histidine (His) is tagged to the terminus of GFP, while GFP is green fluorescent protein, which exhibits bright green fluorescence when exposed to ultraviolet blue light. Comparatively large protein assemblies (e.g. $his_6$-gp10 connector polypeptide, 440 kDa) lead to complexes with more constrained α-CD mobility due to molecular crowding. gp10 is a glycoprotein that contain oligosaccharide chains covalently attached to polypeptide side-chains. In both cases, the adsorbed proteins are presented in all possible orientations due to the dynamic mobility of the threaded Lys-NTA-α-CD to which they are chelated.

Example 3. Quantification of the $Ni^{2+}$ Chelation Capacity of Lys-NTA-α-CD-polyrotaxane Scaffolds $Ni^+$ Activation of NTA-polyrotaxane 4.

Polyrotaxane 4 (100 mg) was dissolved in 1 mL of 20 mM $Ni^{2+}$ solution and the excess $Ni^{2+}$ removed by gel filtration using Sephadex G-25M. After lyophilization, the $Ni^{2+}$:4 complex was obtained as a solid (60 mg).

Preparation of ICP-MS Samples.

$Ni^{2+}$:4 complex (2.6 mg) was digested in 1 mL 70% $HNO_3$ (Aristar Ultra, VWR, West Chester, Pa.) solution for 3 d. The solution was diluted with double deionized water until reaching a concentration of 2% $HNO_3$ (35 mL, 2.25 μM) and then further diluted $10^3$-fold with 2% $HNO_3$ solution. Standard solutions of $Ni^{2+}$ were prepared by diluting a $NiSO_4$ standard solution (Exaxol, Clearwater, Fla.) with 2% $HNO_3$ solution until reaching a final concentration of 10 ppb. Blank 2% $HNO_3$ solutions were prepared by diluting 70% $HNO_3$ (Aristar Ultra) with double deionized water.

To quantify the $Ni^{2+}$ chelation capacity of Lys-NTA-α-CD-polyrotaxane, the total $Ni^{2+}$ content bound to NTA was analyzed by ICP-MS. A solution of 20 mM $NiSO_4$ was added to Lys-NTA-α-CD-polyrotaxane, and the metal bound polyrotaxane is isolated and purified by size exclusion chromatography using Sephadex G-25M resin. ICP-MS (Inductively Coupled Plasma-Mass Spectrometry) analysis of the purified material revealed a $Ni^{2+}$ content corresponding to approximately 19 NTA units per polyrotaxane (assuming a 1:1 $Ni^{2+}$:NTA stoichiometry), a finding that is consistent with the $^1$H-NMR data for this compound.

Example 4. Evaluation of the Protein Adsorption Properties

Figure 2:
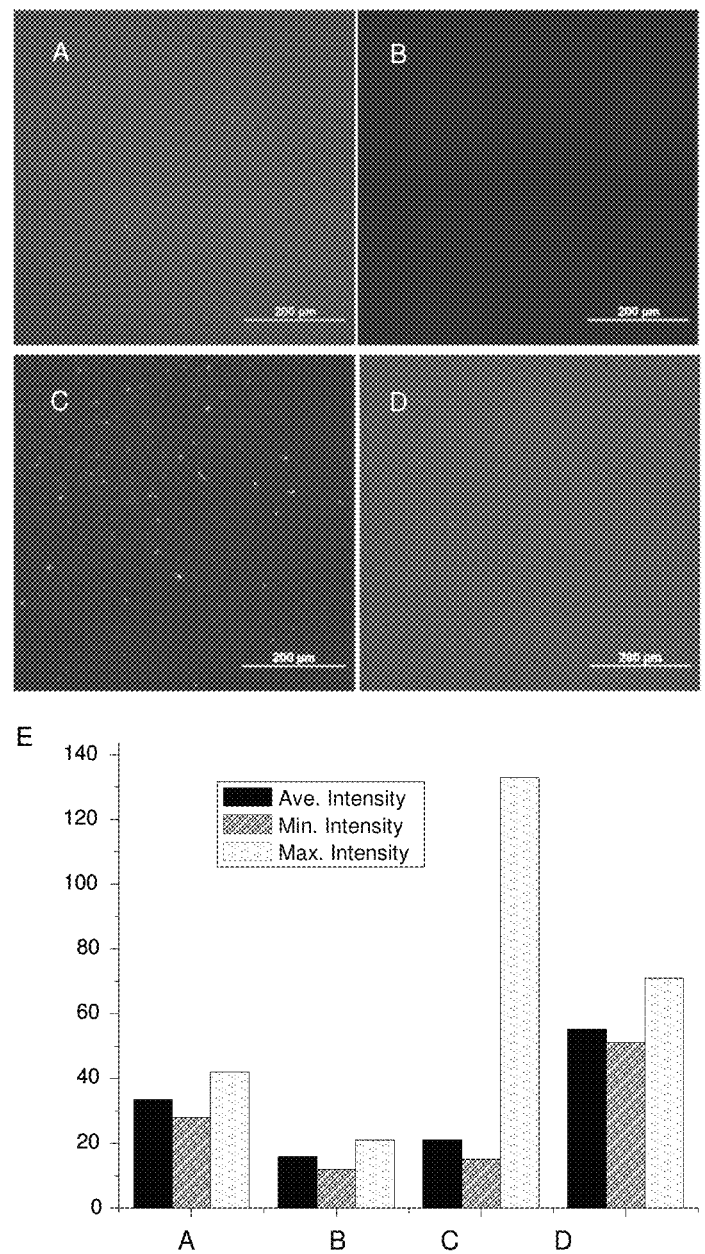
FIG. 2 depicts a fluorescence microscopy analysis of $his_6$-GFP complexation with $Ni^{2+}$-activated compound Lys-NTA-α-CD:PEG (10K) polyrotaxane (Olympus BX51, 10× objective, DP71 CCD camera). (A) $His_6$-GFP (3.0 μM) in 10 mM HEPES buffer at pH 8.0. (B) $Ni^{2+}$:Lys-NTA-α-CD:PEG (10K) polyrotaxane complex (176 nM), (control). (C) Mixture of 3.0 μM $his_6$-GFP and 176 nM $Ni^{2+}$:Lys-NTA-α-CD:PEG (10K) polyrotaxane complex at a 1:1 $his_6$-GFP:α-CD stoichiometry. (D) Same as (C), except that 500 mM imidazole solution was added to (C) to strip the $Ni^{2+}$ from the Lys-NTA-α-CD:PEG10K polyrotaxane complex. (E) Fluorescence intensities of samples (A)-(D), with the average intensity (black bar), minimum intensity (striped bar) and maximum intensity (dotted bar) reported for the CCD counts collected over randomly selected 50 μm×50 μm areas of the corresponding image.

A 3.0 μM $his_6$-GFP solution in 10 mM HEPES buffer at pH 8.0 was prepared and a 10 μL aliquot transferred to a glass slide, covered with a cover slip and examined by fluorescence microscopy (FIG. 2A). In order to visualize the $Ni^{2+}$:4 complex, a solution of $Ni^{2+}$:4 complex without protein (control) was prepared by mixing a 20 mM $NiSO_4$ solution and NTA-polyrotaxane in a 1:1 $Ni^{2+}$:NTA ratio to yield a 176 nM solution which was then transferred to a glass slide, covered with a cover slip and examined by fluorescence microscopy (FIG. 2B). In order to visualize the $his_6$-GFP:$Ni^{2+}$:4 complex, a $his_6$-GFP:$Ni^{2+}$:4 solution was prepared by adding an aliquot of 3.0 µM $his_6$-GFP in 10 mM HEPES buffer at pH 8.0 to a 176 nM $Ni^{2+}$:4 solution to attain 1:1 $his_6$-GFP:α-CD stoichiometry. A 10 µL sample of this solution was transferred to a glass slide, covered with a cover slip and examined by fluorescence microscopy (FIG. 2C). A 10 µL aliquot of 500 mM imidazole was added to the solution in FIG. 2C and a 10 µL sample of this mixture sealed with a cover slip and evaluated by fluorescence microscopy (FIG. 2D). All measurements were made using a Olympus BX51 microscope with a 10× objective and a DP71 CCD camera; the raw data were analyzed using Metavue Software. Final images were converted to grayscale and the brightness and contrast adjusted equally in all images to enhance visualization.

Fluorescence microscopy was used to evaluate the protein adsorption properties of $Ni^{2+}$-activated Lys-NTA-α-CD-polyrotaxane using $his_6$-green fluorescent protein ($his_6$-GFP). FIG. 2A shows a 3.0 µM solution of $his_6$-GFP mounted between two glass slides and viewed by fluorescence microscopy. The appearance of a uniform fluorescence emission across the field of view indicates that GFP does not aggregate under this concentration. FIG. 2B confirms that $Ni^2$-activated Lys-NTA-α-CD-polyrotaxane has no appreciable fluorescence emission under these conditions.

When 10 µL of a 176 nM $Ni^{2+}$-activated Lys-NTA-α-CD-polyrotaxane solution was added to 3.0 µM $his_6$-GFP to produce a 1:1 GFP:α-CD ratio and imaged under identical conditions, many intensely fluorescent spots surrounded by zones of depleted fluorescence intensity were observed (FIG. 2C). It can be inferred from these observations that the regions of high emission intensity are due to locally high GFP concentrations that have been facilitated by the $Ni^{2+}$:Lys-NTA-α-CD:PEG(10K) polyrotaxane complex since GFP does not aggregate under the same conditions in the absence of the polyrotaxane additive.

When a 500 mM imidazole solution was added to disrupt the $Ni^{2+}$:$his_6$-GFP complexation interaction, a re-homogenization of the fluorescence intensity was observed. This observation is consistent with the expectation that excess imidazole should outcompete the his-tags for $Ni^{2+}$ binding, thereby disrupting the $his_6$-GFP:$Ni^{2+}$:Lys-NTA-α-CD-polyrotaxane complex and re-dispersing $his_6$-GFP as a dilute solution of $his_6$-GFP monomer.

Example 5. $His_6$-GFP Aggregation Phenomena in the Presence of $Ni^{2+}$

Figure 3:
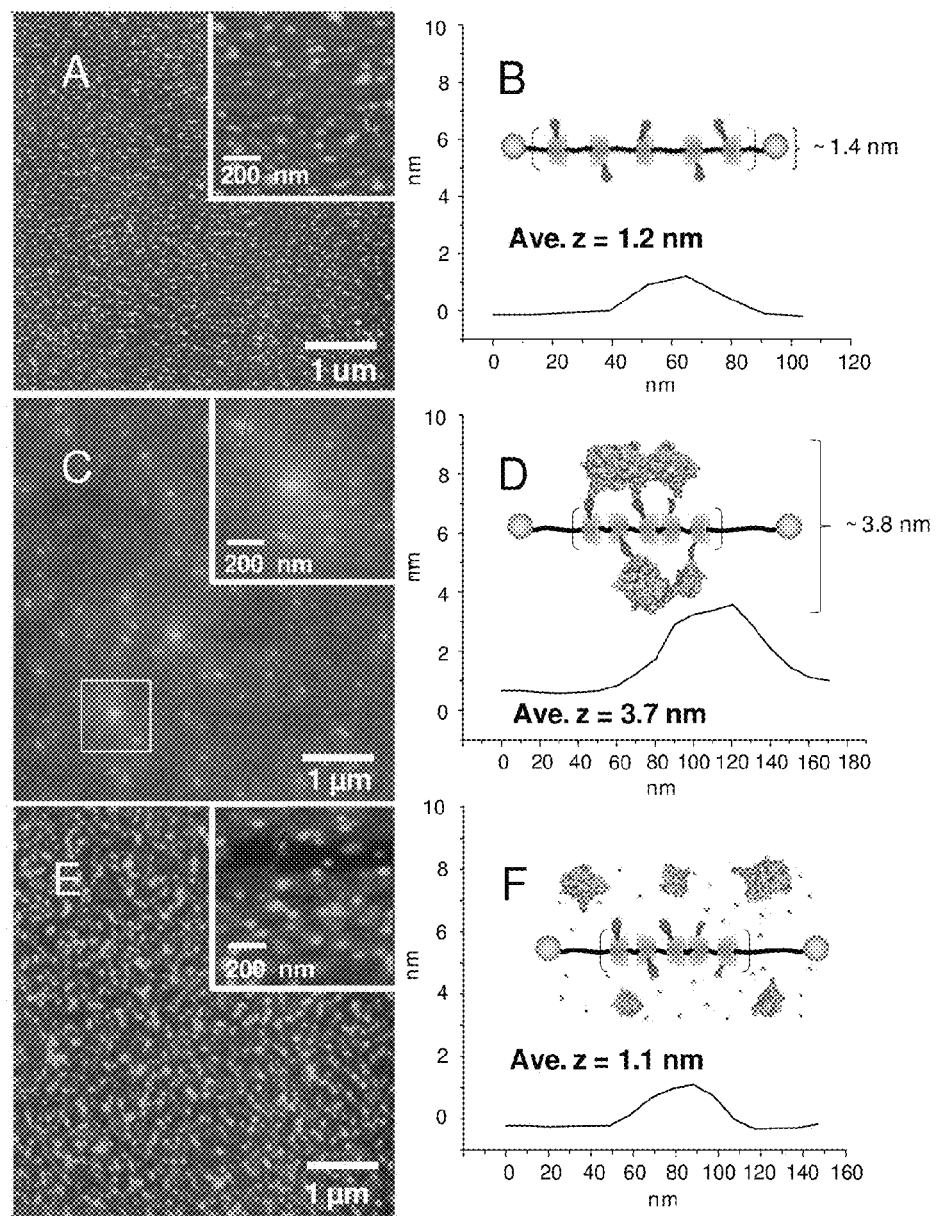
FIG. 3 depicts the tapping mode AFM analysis of: (A, B) 176 nM $Ni^{2+}$:Lys-NTA-α-CD:PEG10K polyrotaxane complex; (C, D) his$_6$-GFP:Ni$^{2+}$:Lys-NTA-α-CD:PEG10K polyrotaxane complex, prepared by mixing 176 nM Ni$^{2+}$:Lys-NTA-α-CD:PEG10K polyrotaxane complex solution with a 3.0 μM his$_6$-GFP solution in 10 mM HEPES buffer at pH 8.0 to attain a 1:1 his$_6$-GFP:α-CD stoichiometry; (E, F) Sample C after addition of 500 mM imidazole solution. Samples were visualized on a Veeco Multimode AFM with a Nanoscope IIIa controller in air at 22° C. The line scans in B, D, & F correspond to the image areas shown in the insets of A, C, & E, respectively.

AFM samples were prepared to further visualize the adsorption properties of the $his_6$-GFP:$Ni^{2+}$:4 complex (FIG. 3A). A 176 nM solution of $Ni^{2+}$:4 complex without protein (control) was prepared by mixing a 20 mM $NiSO_4$ solution and NTA-polyrotaxane in a 1:1 $Ni^{2+}$:NTA ratio to yield a 176 nM solution (FIG. 3B). A 176 nM $Ni^{2+}$:4 complex solution and a 3.0 µM $his_6$-GFP solution in 10 mM HEPES buffer at pH 8.0 were mixed to attain a 1:1 $his_6$-GFP:α-CD stoichiometry on the mica surface (FIG. 3C). A third sample was prepared as described for FIG. 3B, except that a 10 µL aliquot of a 500 mM imidazole solution was added to a 10 µL sample of the solution in FIG. 3B to strip GFP from the polyrotaxane scaffold. The samples were visualized by tapping-mode AFM using a Multimode AFM with a Nanoscope IIIa controller (Veeco) in air at 22° C. The AFM tips (NSC15/AlBS, MikroMasch, USA) used had a typical uncoated probe tip radius of 10 nm or less; the cantilevers had a spring constant of 40 N/m.

AFM studies were performed to provide greater insight into the $his_6$-GFP aggregation phenomena in the presence of $Ni^{2+}$:Lys-NTA-α-CD:PEG10K polyrotaxane complex. AFM images of $Ni^{2+}$:Lys-NTA-α-CD:PEG (10K) polyrotaxane complexes deposited onto mica (FIG. 3A) reveal the presence of features with an average long dimension of 60 nm and an average height of 1.2 nm. After addition of 3.0 µM $his_6$-GFP at a 1:1 GFP:α-CD molar ratio, these objects were transformed into rod-shaped structures with an average to length of ~100 nm (FIG. 3B) and an average height of 3.7 nm, consistent with the adsorption of $his_6$-GFP (GFP is a β-barrel structure that is approximately 4.2 nm high×2.4 nm in diameter) onto the 1.4 nm diameter polyrotaxane scaffold.

Addition of 500 mM imidazole to this solution, followed by incubation for 1 h prior to AFM imaging (FIG. 3C), produced samples that had reverted back to the original morphology with an average diameter of ~40 nm and average height of 1.1 nm. These observations are consistent with our fluorescence microscopy observations and the expected reversible complexation of $his_6$-GFP with the $Ni^{2+}$:Lys-NTA-α-CD:PEG (10K) polyrotaxane complex.

Figure 4:
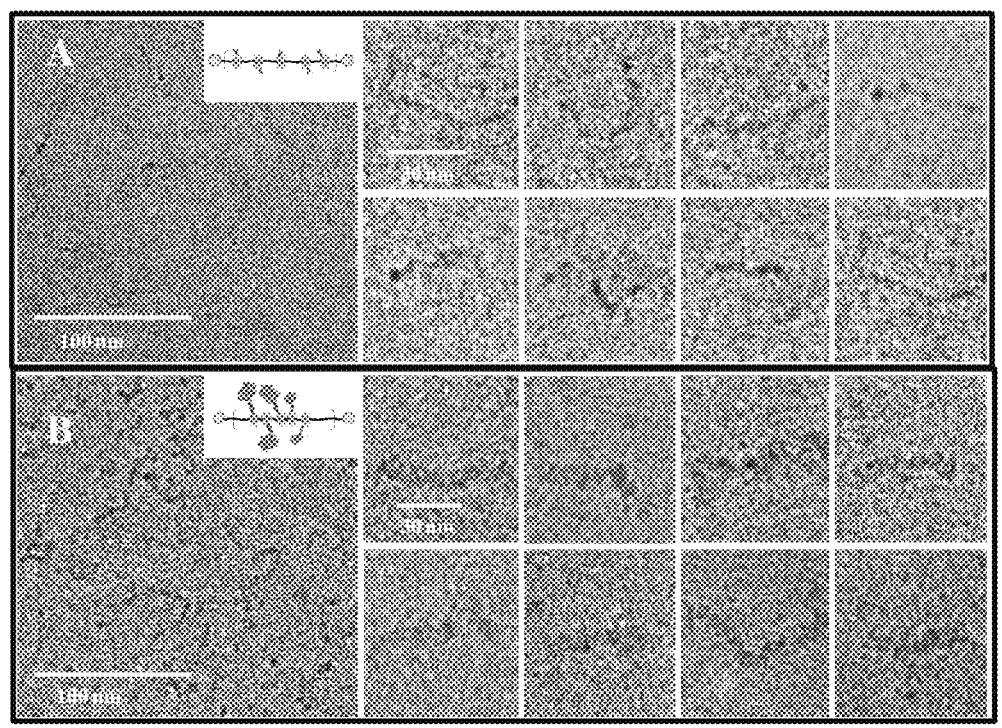
FIG. 4 depicts the cryo-EM imaging of: (A) 1 mM Ni$^{2+}$:Lys-NTA-α-CD:PEG10K polyrotaxane complex; (B) 1 mM his$_6$-GFP:Ni$^{2+}$:Lys-NTA-α-CD:PEG10K polyrotaxane to complex at a 1:1 his$_6$-GFP:α-CD stoichiometry. A gallery of Ni$^{2+}$:Lys-NTA-α-CD:PEG10K polyrotaxane complex features observed at higher magnification appear to the right for samples in the absence (A) and presence (B) of his$_6$-GFP. Samples were spread onto C-Flat™ grids and plunge-frozen in liquid ethane. Images were recorded using a Gatan 1 k×1 k CCD camera on a Philips CM200 transmission electron microscope operating at 40 kV accelerating voltage.

Example 6. $Ni^{2+}$:Lys-NTA-α-CD:PEG (10K) Polyrotaxane Complexes for SPA Applications For cryo-EM imaging, a 176 nM $Ni^{2+}$:4 solution (FIGS. 4A & S2A) and a mixed solution of 176 nM $Ni^{2+}$:4 complex+3.0 µM $his_6$-GFP (1:1 $his_6$-GFP:α-CD stoichiometry) in 10 mM HEPES buffer, pH 8.0 (FIG. 4B) were concentrated to ~1 mM, spread onto C-Flat™ grids then plunge-frozen in liquid ethane. Images were recorded using a Gatan 1 k×1 k charge-coupled device camera on a Philips CM200 TEM.

In order to evaluate the potential of $Ni^{2+}$:Lys-NTA-α-CD:PEG (10K) polyrotaxane complexes for SPA applications, cryo-EM imaging was performed using a small protein target ($his_6$-GFP) that would otherwise be difficult to visualize with this technique due to the combined effects of low EM contrast and extensive protein dispersion. Cryo-EM imaging of $Ni^{2+}$:Lys-NTA-α-CD:PEG (10K) polyrotaxane complex alone (FIG. 4A) showed the presence of many long rod-like structures ranging from ~30-100 nm in length. Cryo-EM imaging of $his_6$-GFP:$Ni^{2+}$:Lys-NTA-α-CD:PEG (10K) polyrotaxane complexes showed the presence of similar rod-like structures, however, these structures were noticeably larger in diameter and exhibited greater electron density than the protein-free control. These observations are in agreement with our fluorescence microscopy and AFM data, providing further support for the hypothesis that $his_6$-GFP chelation to $Ni^{2+}$-activated Lys-NTA-α-CD:PEG (10K) polyrotaxane leads to protein concentration onto the polyrotaxane scaffold. Taking the AFM and cryo-EM to imaging data together, our results suggest that a thin protein layer surrounding the polyrotaxane is formed.

Example 7. Evaluation of the Ability of Large Protein Assemblies to Specifically Adsorb to $Ni^{2+}$:Lys-NTA-α-CD:PEG (10K) Polyrotaxane Complexes TEM was performed using a FEI/Philips CM-10 Bio-Twin instrument and captured on Kodak electron image film (type so-163). Copper 400 mesh grids stabilized with formvar and carbon (Ted Pella Inc. Product No. 01814-F) were glow discharged under a plasma for 30 sec prior to specimen loading. The imaging conditions were: spot size 3, accelerating voltage=80 kV, and apertures of 50 μm (AuF objective) and 200 μm (condenser). All specimens were stained with an aqueous 2% uranyl acetate solution as described below.

A 7.0 μL drop of the specimen was loaded onto the grid and left for 10 sec. Filter paper was used to wick away most of the 7.0 μL drop (leaving just enough to cover the surface of the grid) followed by 3 washing steps with 7.0 μL of double de-ionized water (wicking with filter paper after each wash). After the last washing step with water, 7.0 μL of staining solution was applied to the grid, wicked away with filter paper, and repeated a second time. The specimen was then allowed to dry before imaging.

Figure 5:
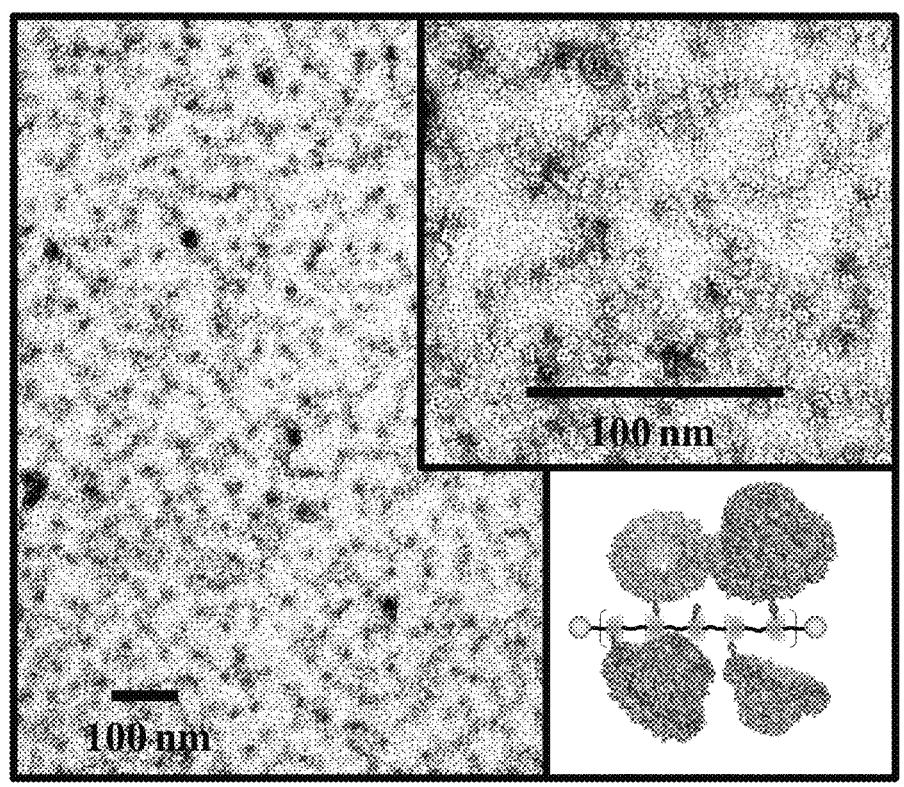
FIG. 5 depicts the negative-stain TEM imaging of his$_6$-gp10:Ni$^{2+}$:Lys-NTA-α-CD:PEG (10K) polyrotaxane complex. Images were taken with FEI/Philips CM-10 Bio-Twin instrument using glow discharged carbon-coated formvar copper 400 mesh grids (80 kV accelerating voltage) stained with a 2% UO$_2$(OAc)$_2$ solution.
Figure 6:
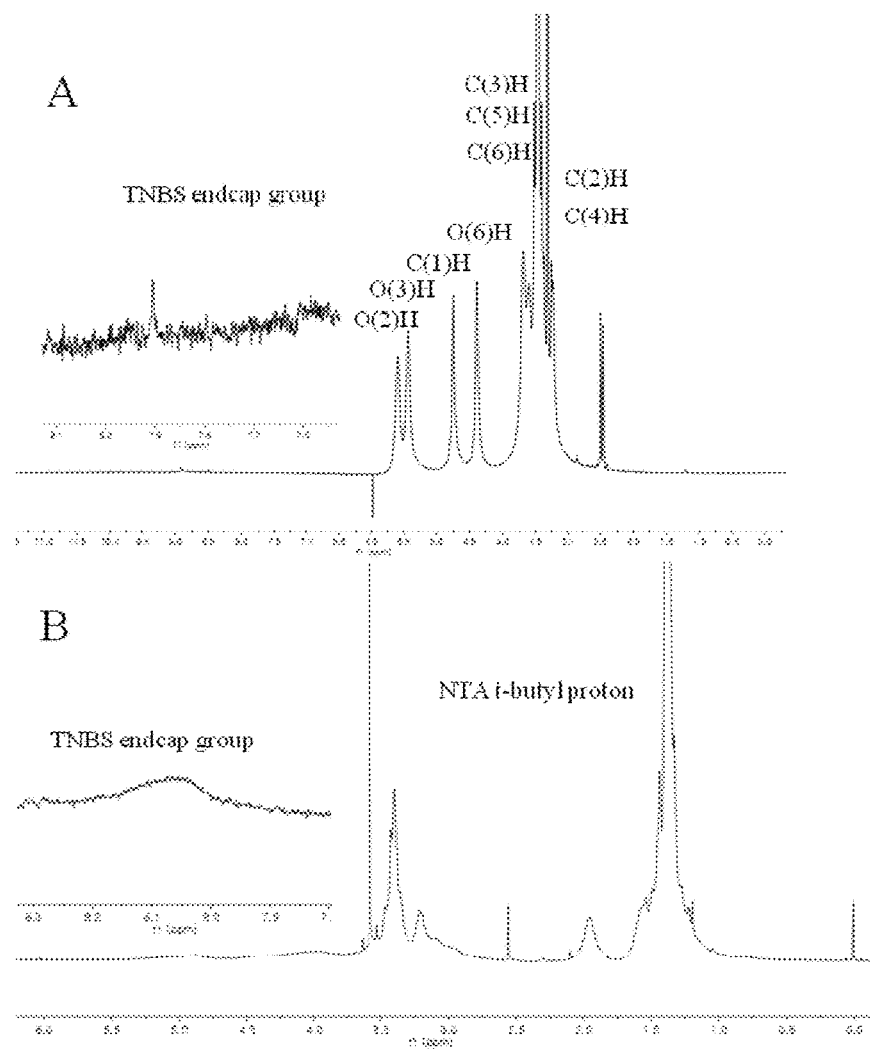
FIG. 6 shows 400 MHz $^1$H NMR spectra of (A) Polyrotaxane 1, and (B) t-Butyl NTA-polyrotaxane (3) in DMSO-d$_6$.

As indicated in FIG. 5, negative stain TEM was performed at the Purdue University Life Science Microscopy Facility. Images were taken on the FEI/Philips CM-10 Bio-Twin instrument and captured on Kodak electron image film (type: so-163 films). Copper 400 mesh grids stabilized with formvar and carbon (Ted Pella Inc. Product No. 01814-F) were used. All grids used for imaging were glow discharged under plasma for 30 sec prior to specimen loading. The microscope conditions of the microscope were: spot size 3, accelerating voltage of 80 kV, objective aperture (AuF) and condenser aperture were 50 μm and 200 μm, respectively. All specimens were stained with a 2% uranyl acetate (aq) solution as described below. The specimen consisted of his$_6$-gp-10+polyrotaxane-NTA+Ni$^{2+}$. A 7.0 μL drop of the specimen was loaded onto the grid and left for 10 sec. Filter paper was used to wick away most of the 7.0 μL drop (leaving just enough to cover the surface of the grid) followed by 3 washing steps with 7.0 μL of double de-ionized water (wicking with filter paper after each wash). After the last washing step with water, 7.0 μL of staining solution was applied to the grid, wicked to away with filter paper, and repeated a second time. The specimen was then allowed to dry before imaging.

In order to evaluate the ability of large protein assemblies to specifically adsorb to Ni$^2$-activated NTA-polyrotaxanes, we performed negative stain TEM imaging of Ni$^{2+}$:Lys-NTA-α-CD:PEG (10K) polyrotaxane complexes treated with his-tagged bacteriophage phi29 connector protein assemblies (his$_6$-gp10) at a 1:1 his$_6$-gp10:α-CD ratio. This 440 kDa protein dodecamer of gp10 connects the phage head to the ATP-driven motor that is responsible for DNA translocation and packaging during the formation of mature virion particles. TEM images (FIG. 5) revealed the presence of many round pore-containing objects whose dimensions are consistent with phi29 connector protein assemblies; these features were presented in the same roughly linear arrangement seen for the Ni$^2$-activated NTA-polyrotaxane control. It can be inferred from these observations that his$_6$-gp10 is binding to the Ni$^{2+}$:Lys-NTA-α-CD:PEG (10K) polyrotaxane scaffold in a manner similar to his$_6$-GFP, except that the protein is not as densely packed along the polyrotaxane scaffold due to the spatial demands of the much larger phi29 connector array.

Figure 11:
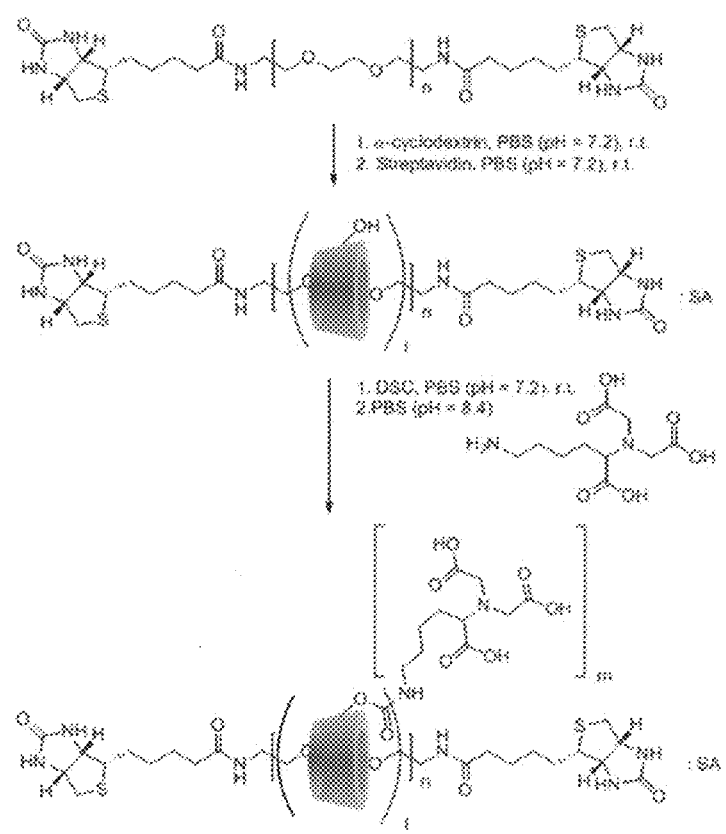
FIG. 11 depicts Scheme 2 for synthesis of PEG-10K-bisamine.

Example 8. Synthesis of NTA-modified-α-CD:biotin-PEG-biotin:SAPolyrotaxane Hydrogel (FIG. 11)

Materials

Bifunctional PEG's and multi-armed PEG's were purchased from Nanocs (Boston, Mass.) and used as received. Streptavidin was purchased from Thermo Scientific as a lyophilized powder and reconstituted and stored in 20 mM potassium phosphate buffer (pH=6.5) at a concentration of 10 mg/mL. Disuccinimidyl carbonate (DSC) was purchased from Aldrich. Lysine-NTA was prepared following a previously reported method. Holey carbon-coated C-Flat™ TEM grids (400 mesh) were purchased from Electron Microscopy Sciences.

Synthesis of α-CD:biotin-PEG-biotin:SA-Polyrotaxane Hydrogel

α-Cyclodextrin (α-CD) (2.0 g, 2 mmol) was fully dissolved in 15 mL of PBS (pH=7.2) before addition of biotin-PEG-biotin of appropriate molecular weight (177 mg). The mixture was sonicated for 30 min at 20° C. and the resulting white gel-like substance stored at 20° C. for 12 h. Streptavidin was added and the slurry stirred gently for 12 h. The reaction mixture was washed with water before dialyzing the product (molecular weight cut-off 6,000-8,000) against H$_2$O for 2 d. The retained dialysate was then lyophilized to give α-CD:biotin-PEG-biotin:SA-Polyrotaxane Hydrogel.

Synthesis of NTA-modified-α-CD:biotin-PEG-biotin:SA-Polyrotaxane Hydrogel

α-CD:biotin-PEG-biotin:SA-Polyrotaxane Hydrogel was suspended in 5 mL of PBS (pH=7.2). To this suspension was added Lysine-NTA that had been preactivated with CDI (1 equiv/mol Lysine-NTA) and the suspension stirred with the activated Lysine-NTA derivative for 12 h at room temperature. The resulting suspension was dialyzed (molecular weight cut-off 6,000-8,000) against H$_2$O for 2 d. The retained dialysate was then lyophilized to give NTA-modified-α-CD:biotin-PEG-biotin:SA-Polyrotaxane Hydrogel.

Synthesis of NTA-Modified-α-CD:biotin-PEG-biotin:SA-Polyrotaxane Hydrogel Supported on TEM Grids α-CD:biotin-PEG-biotin pseudopolyrotaxane was suspended in 5 mL of PBS (pH=7.2). A second solution containing SA in 300 mM phosphate buffered saline at pH 7.2 was added to the C flat TEM grid and the excess blotted away with filter paper, leaving a thin film of SA solution in between the grid bars. To this grid entrapped solution was added the α-CD:biotin-PEG-biotin pseudopolyrotaxane solution, such that gentle addition produced minimal turbulent mixing of the two aqueous solutions. The samples were allowed to mix for 12 h via diffusion at the interface between the two solutions to produce a network polymer structure. The network material was then treated with Lysine-NTA that had been preactivated with CDI (1 equiv/mol Lysine-NTA) and the suspension layered onto the network structure with a subsequent reaction period of 12 h at room temperature. The resulting network structure was rinsed extensively with deionized water to give the NTA-modified-α-CD:biotin-PEG-biotin:SA-Polyrotaxane Hydrogels supported on TEM grids.

Figure 12:
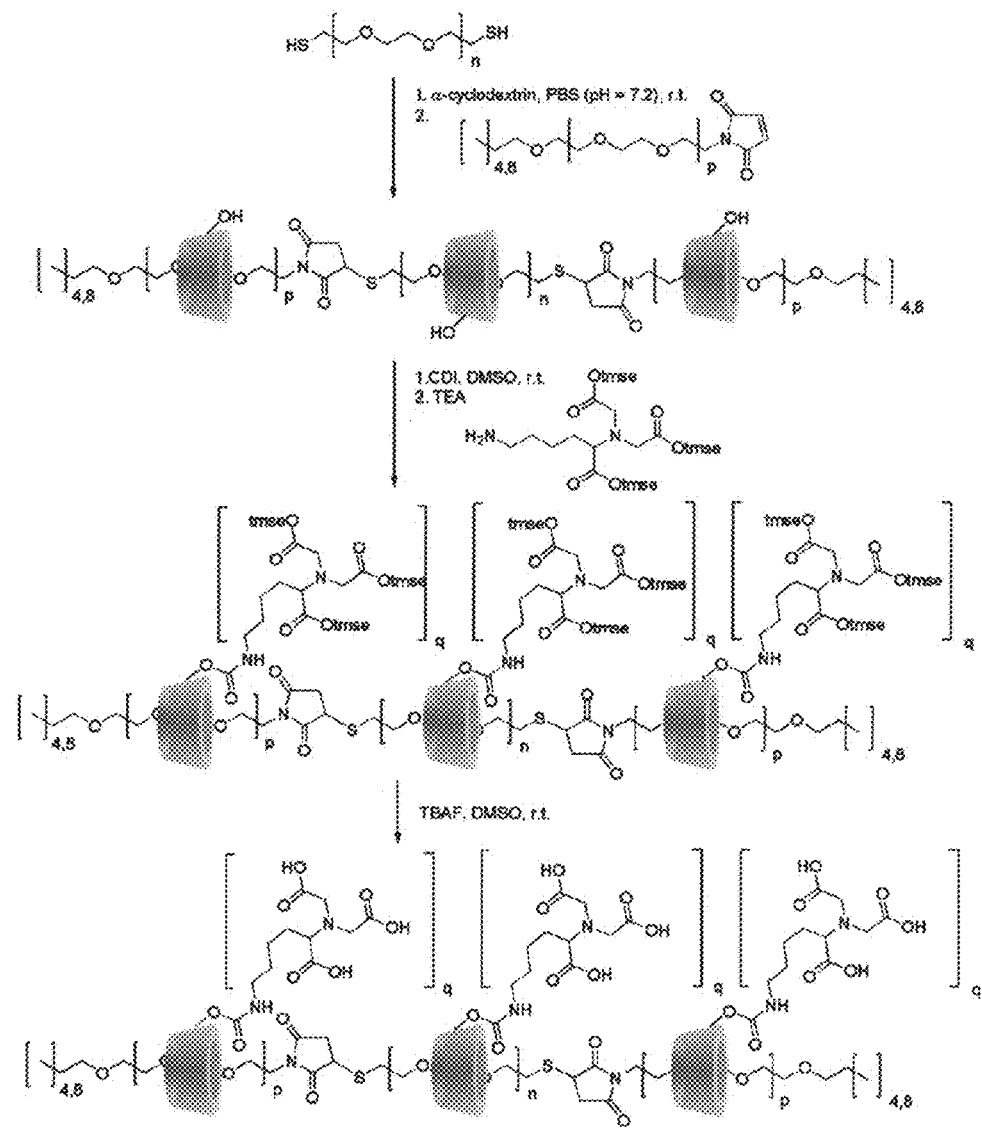
FIG. 12 depicts Scheme 3 for synthesis of NTA-modified-α-CD:biotin-PEG-biotin:SApolyrotaxane hydrogel.

Example 9. Synthesis of NTA-modified-α-CD:HS-PEG-SH:4,8-arm-PEG-MAL-Polyrotaxane Hydrogel (FIG. 12)

Synthesis of NTA-Modified-α-CD:biotin-PEG-biotin:SA-Polyrotaxane Hydrogel

α-CD:biotin-PEG-biotin-pseudopolyrotaxane was suspended in 5 mL of PBS (pH=7.2). A second solution containing SA in 300 mM phosphate buffered saline at pH 7.2 was added to the C flat TEM grid and the excess blotted away with filter paper, leaving a thin film of SA solution in between the grid bars. To this grid entrapped solution was added the α-CD:biotin-PEG-biotin-pseudopolyrotaxane solution, such that gentle addition produced minimal turbulent mixing of the two aqueous solutions. The samples were allowed to mix for 12 h via diffusion at the interface between the two solutions to produce a network polymer structure. The network material was then treated with Lysine-NTA that had been preactivated with CDI (1 equiv/mol Lysine-NTA) and the suspension layered onto the network structure with a subsequent reaction period of 12 h at room temperature. The resulting network structure was rinsed extensively with deionized water to give the NTA-modified-α-CD:biotin-PEG-biotin:SA-Polyrotaxane Hydrogels supported on TEM grids.

Synthesis of
α-CD:HS-PEG-SH:Multi-arm-PEG-MAL-Polyrotaxane
Hydrogel

α-CD (2.0 g, 2 mmol) was fully dissolved in 15 mL of PBS (pH=7.2) before addition of HS-PEG-SH (177 mg) of appropriate molecular weight. The mixture was sonicated for 30 min at 20° C. and the resulting white gel-like substance stored at 20° C. for 12 h. Multi-armed-PEG-MAL was added and the slurry stirred for 12 h. The reaction mixture was washed with water before dialyzing the product (molecular weight cut-off 6,000-8,000) against $H_2O$ for 2 d. The retained dialysate was then lyophilized to give α-CD:HS-PEG-SH:Multi-armed-PEG-MAL-Polyrotaxane Hydrogel.

Synthesis of NTA-(Otmse)$_3$-Modified-α-CD:HS-PEG-SH:Multi-arm-PEG-MAL-Polyrotaxane
Hydrogel α-CD:HS-PEG-SH:Multi-armed-PEG-MAL-Polyrotaxane Hydrogel was dispersed in DMSO. To this was added CDI (10 equiv/mol α-CD) and the solution was stirred at room temperature for 4 h. Next, $H_2N$-NTA-(Otmse)$_3$ was added (10 equiv/mol α-CD) and the resulting solution was stirred for 24 h. The solution was then dialyzed (molecular weight cut-off 6,000-8,000) against DMSO for 1 d then $H_2O$ for 2 d and lyophilized to give NTA-(Otmse)$_3$-modified-α-CD:HS-PEG-SH:Multi-arm-PEG-MAL-Polyrotaxane Hydrogel.

Synthesis of NTA-Modified-α-CD:HS-PEG-SH:
Multi-arm-PEG-MAL-Polyrotaxane Hydrogel NTA-(Otmse)$_3$-modified-α-CD:HS-PEG-SH:Multi-arm-PEG-MAL-Polyrotaxane Hydrogel was dispersed in a DMSO solution (15 mL) containing 1.0 M tetrabutylammoniumfluoride (TBAF) and the suspension stirred at room temperature for 6 h. The solution was then dialyzed (molecular weight cut-off 6,000-8,000) against DMSO for 1 d then $H_2O$ for 2 d and lyophilized to give NTA-modified-α-CD:HS-PEG-SH:Multi-arm-PEG-MAL-Polyrotaxane Hydrogel.

Synthesis of
α-CD:HS-PEG-SH:Multi-arm-PEG-MAL-Polyrotaxane
Hydrogel via Interfacial Polymerization α-CD (2.0 g, 2 mmol) was fully dissolved in 15 mL of PBS (pH=7.2) before addition of HS-PEG-SH (177 mg) of appropriate molecular weight. The mixture was sonicated for 30 min at 20° C. and the resulting white gel-like substance stored at 20° C. for 12 h. Multi-armed-PEG-MAL was dissolved in DMSO and the solution added to C flat TEM grids; the to excess solution was wicked away with filter paper, leaving a thin film of grid-entrapped solution between the grid bars. The aqueous suspension of α-CD:HS-PEG-SH was added to the TEM grid and the samples allowed to react at the $H_2O$-DMSO interface for 12 h. The reaction mixture was then gently rinsed with water before reaction with activated Lysine-NTA as above to give α-CD:HS-PEG-SH:Multi-armed-PEG-MAL-Polyrotaxane Hydrogel supported on TEM grids.

Example 10. Deposition of Polyrotaxane Hydrogels onto TEM Grids

The polyrotaxane hydrogel networks produced via solution-phase crosslinking were deposited onto C flat TEM grids via stepwise addition of an aliquot of hydrogel to the grid, followed by centrifugal deposition of the network onto the grid using a Beckman centrifuge fitted with a rotor designed for processing TEM grids. This process was repeated until a 200 nm thick film had been deposited onto the grid as determined by FIB-SEM analysis.

Example 11. Preparation of Linear NTA-polyrotaxane Samples for Cryo-EM

Figure 7:
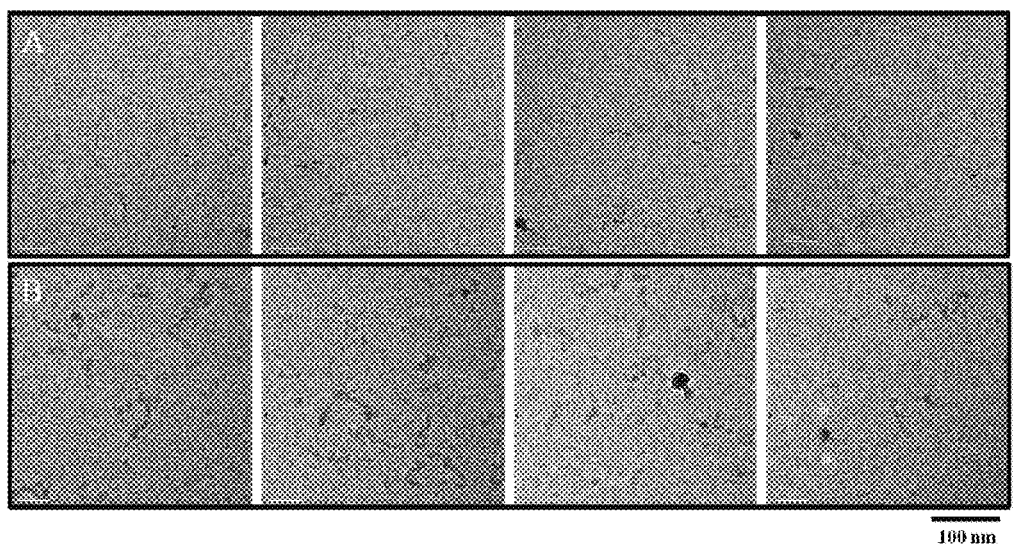
FIG. 7 depicts cryo-EM images of (A) Ni$^{2+}$:NTA-polyrotaxane 4, and (B) his$_6$-GFP:Ni$^{2+}$:NTA-polyrotaxane 4 complex.

For cryo-EM imaging, a 176 nM $Ni^{2+}$:NTA-modified PEG-10K polyrotaxane solution (FIGS. 4A & 7A) and a mixed solution of 176 nM $Ni^{2+}$:NTA-modified PEG-10K polyrotaxane complex+3.0 µM his$_6$-tagged protein (1:1 his$_6$:α-CD stoichiometry) in 10 mM HEPES buffer, pH 8.0 (FIGS. 4B & 7B) were concentrated to ~1 mM, spread onto C-Flat™ grids then plunge-frozen in liquid ethane. Images were recorded using a Gatan 4 k×4 k charge-coupled device camera on a Philips CM-200 TEM.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A polyrotaxane comprising a plurality of macrocyclic molecules, a linear axle molecule threading through the macrocyclic molecules, and a capping group at each end of the linear axle molecule, wherein one or more of the macrocyclic molecules comprise an affinity binding group and wherein the macrocyclic molecules are laterally and rotationally mobile along the linear axle molecule, wherein the affinity binding group is a metal chelate having a chelating agent moiety and a metal ion, wherein the capping group is linked to the linear moiety through a bond, wherein said metal ion is $Ni^{2+}$, and wherein the polyrotaxane has the following structure

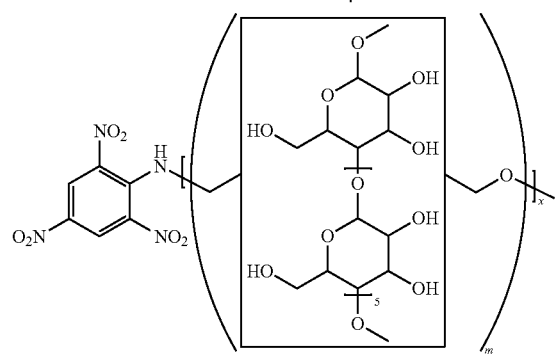

-continued

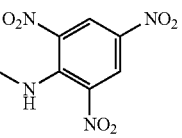

wherein x is 113; m is 17; and n is 1.1.

2. A method of characterizing or determining a three-dimensional structure of a biological molecule, comprising the steps of
   (a) contacting a polyrotaxane with the biological molecule to form a complex;
   (b) subjecting the complex to cryogenic electron microscopy; and
   (c) analyzing data collected from the cryogenic electron microscopy experiment wherein said polyrotaxane comprises a plurality of macrocyclic molecules, a linear axle molecule threading through the macrocyclic molecules, and a capping group at each end of the linear axle molecule, wherein one or more of the macrocyclic molecules comprise an affinity binding group and wherein the macrocyclic molecules are laterally and rotationally mobile along the linear axle molecule, wherein the affinity binding group is a metal chelate having a chelating agent moiety and a metal ion, wherein the capping group is linked to the linear moiety through a bond, and wherein said metal ion is $Ni^{2+}$;

wherein the polyrotaxane has the following structure

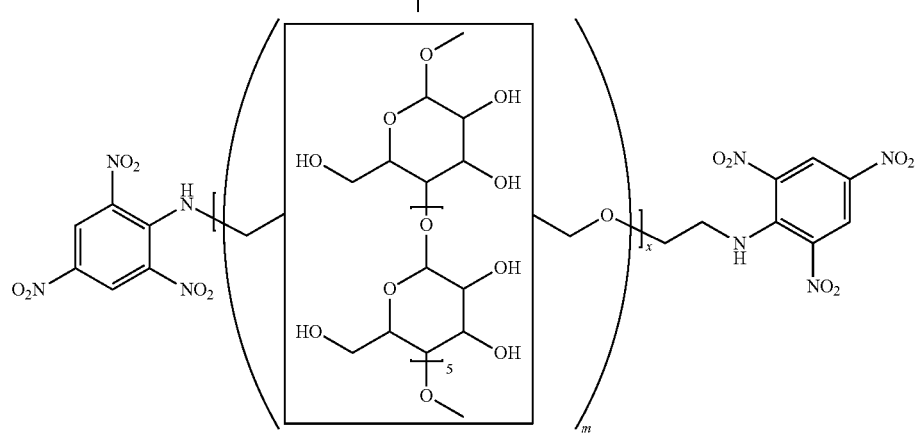

wherein x is 113; m is 17; and n is 1.1.

3. The method of claim 2, wherein the biological molecule is a protein, a lipid, a nucleic acid, an oligosaccharide, or a complex thereof.

4. The method of claim 2, wherein the biological molecule is a protein or a complex thereof.

5. The method of claim 2, wherein the ratio of the number of the biological molecule to the number of the macrocyclic molecules is from about 1:6 to about 1:1.

6. The method of claim 2, wherein the polyrotaxane is a crosslinked polyrotaxane.

7. The method of claim 6, wherein the crosslinked polyrotaxane is in the form of a thin membrane for specific capture of affinity tagged biological molecules.

8. The method of claim 7, wherein the thin membrane is deposited on TEM grids.

* * * * *